United States Patent [19]

Kraus et al.

[11] Patent Number: 5,599,678
[45] Date of Patent: Feb. 4, 1997

[54] ANTIBODIES WHICH REACT WITH FIBRINOGEN FRAGMENTS E1, E2 AND E3 AND METHODS OF THEIR USE

[75] Inventors: Michael Kraus, Marburg; Werner Stüber, Lahntal, both of Germany

[73] Assignee: Behringwerke Aktiengesellschaft, Marburg, Germany

[21] Appl. No.: 166,930

[22] Filed: Dec. 15, 1993

[30] Foreign Application Priority Data

Dec. 17, 1992 [DE] Germany ................... 42 42 736.3

[51] Int. Cl.$^6$ ........................ G01N 33/53; C07K 16/36
[52] U.S. Cl. ..................... 435/7.9; 435/7.92; 435/7.93; 435/7.94; 435/7.95; 435/13; 436/518; 436/536; 436/537; 436/538; 530/387.9; 530/388.25; 530/389.3; 530/391.1; 530/391.3
[58] Field of Search ..................... 435/7.9, 7.92, 435/7.93, 7.94, 7.95, 13, 70.2, 240.27; 530/387.1, 387.9, 388.25, 391.1, 389.3, 391.3; 436/518, 536, 909, 537, 538

[56] References Cited

U.S. PATENT DOCUMENTS 4,960,712  10/1990  Theofilopoulos et al. ............. 436/501

FOREIGN PATENT DOCUMENTS

3701812A1  8/1988  Germany.
WO86/01298  2/1986  WIPO.

OTHER PUBLICATIONS

E. F. Plow et al., "Localization and Characterization of the Cleavage–associated Neoantigen Locus in the E Domain of Fibrinogen," The Journal of Biological Chemistry, vol. 254, No. 3, (Feb. 10, 1979) pp. 672–678.
J. P. Chen et al., "Radioimmunoassay of fragment E–related neoantigen: validation studies and clinical application," British Journal of Haematology, vol. 57, (1984) pp. 133–144.
P. W. Koppert et al., "A Monoclonal Antibody–Based Enzyme Immunoassay for Fibrin Degradation Products in Plasma," Thrombosis and Haemostasis, vol. 59, No. 2, (Apr. 8, 1988) pp. 310–315.
D. W. Chung et al., "Nucleotide Sequences of the Three Genes Coding for Human Fibrinogen," Adv. Exp. Med. Biol., vol. 281 (1990) pp. 39–48.
N. E. Kirschbaum et al., "A Unique Proteolytic Fragment of Human Fibrinogen Containing the Aα Cooh–terminal Domain of the Native Molecule," The Journal of Biological Chemistry, vol. 265 (Aug. 15, 1990) pp. 13669–13676.
"Chemical Coupling of Peptides and Proteins to Polysaccharides by Means of Cyanogen Halides", Axen et al., Nature, 214:1302–1304 (1967).
"A Rapid, Simple, Sensitive Method for Measuring Fibrinolytic Split Products in Human Serum", Merskey et al., Proc. Soc. Exp. Biol. Med., 131:871–875 (1969).
"Peroxidase–Labeled Anibody—A New Method of Conjugation", Nakane et al., The Journal of Histochemistry and Cytochemistry, 22(12):1084–1091 (1974).

"Physical Biochemistry—*Applications to Biochemistry and Molecular Biology*", Freifelder, D., Saka W. H. Freeman and Company, p. 19:236(1976).
"Binding Phenomena of Isolated Unique Plasmic Degradation Products of Human Cross–linked Fibrin", Olexa et al., The Journal of Biological Chemistry, 254(11):4925–4932 (1979).
"Monoclonal Antibodies to a Synthetic Fibrin–Like Peptide Bind to Human Fibrin but No Fibrinogen", Hui et al., Science, 222:1129–1132 (1983).
"A Quantitative Automated Immunoassay for Fibrinogen/ Fibrin Degradation Products", Schifreen et al., Clinical Chemistry, 31(9):1468–1473 (1985).
"Unreliabiltiy of Current Serum Fibrin Degradation Product (FDP) Assays", Gaffney et al., Thrombosis and Haemostasis, 53(3):301–302 (1985).
"Monoclonal Antibodies Against Fibrinogen, Fibrin and Their Fragments", Gaffney et al., Thrombosis and Haemostasis, 54(3):733–734 (1985).
"Plasma Assays of Fibrinogen/Fibrin Degradation Products and Their Clinical Relevance", Nieuwenhuizen, W., Fibrinogen 2. Biochemistry physiology and clinical relevance, Lowe et al., Eds., 173–180(1987).
"A Monoclonal Antibody–Based Enzyme Immunoassay for Fibrin Degradatiion Products in Plasma", Koppert et al., Thrombosis and Haemostasis, 59(2):310–315(1988).
"Automated Nephelometric Immunoassays With Novel Shell/Core Particles", Kapmeyer et al., Journal of Clinical Laboratory Analysis, 2:76–83(1988).
Henschen, A., et al., "Covalent Structure of Fibrinogen" Annals of the New York Academy of Science 408:28–43, 1983.
Rose, N. R., et al., eds. Manual of Clinical Laboratory Immunology, Washington, D.C.: American Society for Microbiology, 1986, pp. 24–42 and 99–108.
Sevier, E. D. et al. "Monoclonal Antibodies in Clinical Immunology", 27(11) :1797–1806, 1981.
P. Tijssen, Practice and Theory of Enzyme Immunoassays, In: Laboratory Techniques in Biochemistry and Molecular Biology vol. 15 New York: Elsevier, 1985, pp. 108–109.
J. P. Chen et al. "Radioimmunoassay of Fragment E–related neoantigen: Validation Studies and Clinical Applications" Journal of Haematology 57: 133–144, 1984.
S. A. Olexa et al. "Structure of Fragment E species from Human Cross–linked Fibrin" Biochemistry 21:6139–6145, 1981.
T. M. Price, et al. "Shadow–cast electron–microscopy of fibrinogen with antibody fragment bound to specific regions Proceedings of the National Academy of Science USA" 78(1) 200–204, 1981.

*Primary Examiner*—Christine Chan
*Assistant Examiner*—Lora M. Green
*Attorney, Agent, or Firm*—Finnegan, Henderson, Farabow, Garrett & Dunner, L.L.P.

[57] ABSTRACT

The invention relates to antibodies which react with fibrinogen fragments E1, E2 and E3 raised by immunizing with a peptide. The invention also relates to assay methods for proteins containing an epitope which is common to fibrinogen fragments E1, E2 and E3 using these antibodies.

13 Claims, 16 Drawing Sheets

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( x i ) SEQUENCE DESCRIPTION: SEQ ID NO:1:

Leu Phe Glu Tyr Gln Lys
1               5

( 2 ) INFORMATION FOR SEQ ID NO:2:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( x i ) SEQUENCE DESCRIPTION: SEQ ID NO:2:

Tyr Met Tyr Leu Leu Lys
1               5

( 2 ) INFORMATION FOR SEQ ID NO:3:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( x i ) SEQUENCE DESCRIPTION: SEQ ID NO:3:

Val Lys Glu Leu Ile Lys
1               5

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
His  Gln  Val  Glu  Asn  Lys
1                 5
```

( 2 ) INFORMATION FOR SEQ ID NO:5:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Asn  Lys  Leu  Lys  Asn  Ser  Leu  Phe  Glu  Tyr  Gln  Lys
1                 5                           10
```

( 2 ) INFORMATION FOR SEQ ID NO:6:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Ser  Ser  Ser  Ser  Phe  Gln  Tyr  Met  Tyr  Leu  Leu  Lys
1                 5                           10
```

( 2 ) INFORMATION FOR SEQ ID NO:7:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Glu  Asn  Lys  Thr  Ser  Gln  Val  Lys  Gln  Leu  Ile  Lys
1                 5                           10
```

( 2 ) INFORMATION FOR SEQ ID NO:8:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
Ser  Leu  Glu  Asp  Ile  Leu  His  Gln  Val  Glu  Asn  Lys
1                 5                           10
```

( 2 ) INFORMATION FOR SEQ ID NO:9:

( i ) SEQUENCE CHARACTERISTICS:
        ( A ) LENGTH: 55 amino acids (B) TYPE: amino acid
(D) TOPOLOGY: linear (ii) MOLECULE TYPE: peptide (xi) SEQUENCE DESCRIPTION: SEQ ID NO:9:

```
His Glu Ser Ala Cys Lys Asp Ser Asp Trp Pro Phe Cys Ser Asp Glu
 1               5                  10                  15
Asp Trp Asn Tyr Lys Cys Pro Ser Gly Cys Arg Met Lys Gly Leu Ile
            20                  25                  30
Asp Glu Val Asn Gln Asp Phe Thr Asn Arg Ile Asn Lys Leu Lys Asn
        35                  40                  45
Ser Leu Phe Glu Tyr Gln Lys
    50              55
```

(2) INFORMATION FOR SEQ ID NO:10:

(i) SEQUENCE CHARACTERISTICS:
    (A) LENGTH: 69 amino acids
    (B) TYPE: amino acid
    (D) TOPOLOGY: linear (ii) MOLECULE TYPE: peptide (xi) SEQUENCE DESCRIPTION: SEQ ID NO:10:

```
Lys Val Glu Arg Lys Ala Pro Asp Ala Gly Gly Cys Leu His Ala Asp
 1               5                  10                  15
Pro Asp Leu Gly Val Leu Cys Pro Thr Gly Cys Gln Leu Gln Glu Ala
            20                  25                  30
Leu Leu Gln Gln Glu Arg Pro Ile Arg Asn Ser Val Asp Glu Leu Asn
        35                  40                  45
Asn Asn Val Glu Ala Val Ser Gln Thr Ser Ser Ser Ser Phe Gln Tyr
    50                  55                  60
Met Tyr Leu Leu Lys
65
```

(2) INFORMATION FOR SEQ ID NO:11:

(i) SEQUENCE CHARACTERISTICS:
    (A) LENGTH: 62 amino acids
    (B) TYPE: amino acid
    (D) TOPOLOGY: linear (ii) MOLECULE TYPE: peptide (xi) SEQUENCE DESCRIPTION: SEQ ID NO:11:

```
Tyr Val Ala Thr Arg Asp Asn Cys Cys Ile Leu Asp Glu Arg Phe Gly
 1               5                  10                  15
Ser Tyr Cys Pro Thr Thr Cys Gly Ile Ala Asp Phe Leu Ser Thr Tyr
            20                  25                  30
Gln Thr Lys Val Asp Lys Asp Leu Gln Ser Leu Glu Asp Ile Leu His
        35                  40                  45
Gln Val Glu Asn Lys Thr Ser Glu Val Lys Gln Leu Ile Lys
    50                  55                  60
```

(2) INFORMATION FOR SEQ ID NO:12:

(i) SEQUENCE CHARACTERISTICS:
    (A) LENGTH: 53 amino acids
    (B) TYPE: amino acid
    (D) TOPOLOGY: linear (ii) MOLECULE TYPE: peptide ( x i ) SEQUENCE DESCRIPTION: SEQ ID NO:12:

Tyr Val Ala Thr Arg Asp Asn Cys Cys Ile Leu Asp Glu Arg Phe Gly
1               5                   10                  15

Ser Tyr Cys Pro Thr Thr Cys Gly Ile Ala Asp Phe Leu Ser Thr Tyr
            20              25                  30

Gln Thr Lys Val Asp Lys Asp Leu Gln Ser Leu Glu Asp Ile Leu His
        35              40                  45

Gln Val Glu Asn Lys
        50

( 2 ) INFORMATION FOR SEQ ID NO:13:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

Val Asp Lys Asp Leu Gln Ser Leu Glu Asp Ile Leu His Gln Val Glu
1               5                   10                  15

Asn Lys ( 2 ) INFORMATION FOR SEQ ID NO:14:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

Cys Val Asp Lys Asp Leu Gln Ser Leu Glu Asp Ile Leu His Gln Val
1               5                   10                  15

Glu Asn Lys ( 2 ) INFORMATION FOR SEQ ID NO:15:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

Cys His Gln Val Glu Asn Lys
1               5

( 2 ) INFORMATION FOR SEQ ID NO:16:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

Cys Asp Ile Leu His Gln Val
1               5

( 2 ) INFORMATION FOR SEQ ID NO:17:

(i) SEQUENCE CHARACTERISTICS:
  (A) LENGTH: 7 amino acids
  (B) TYPE: amino acid
  (D) TOPOLOGY: linear (ii) MOLECULE TYPE: peptide (xi) SEQUENCE DESCRIPTION: SEQ ID NO:17:

Cys  Ser  Leu  Glu  Asp  Ile  Leu
1                    5

(2) INFORMATION FOR SEQ ID NO:18:

(i) SEQUENCE CHARACTERISTICS:
  (A) LENGTH: 7 amino acids
  (B) TYPE: amino acid
  (D) TOPOLOGY: linear (ii) MOLECULE TYPE: peptide (xi) SEQUENCE DESCRIPTION: SEQ ID NO:18:

Cys  Asp  Leu  Gln  Ser  Leu  Glu
1                    5

(2) INFORMATION FOR SEQ ID NO:19:

(i) SEQUENCE CHARACTERISTICS:
  (A) LENGTH: 7 amino acids
  (B) TYPE: amino acid
  (D) TOPOLOGY: linear (ii) MOLECULE TYPE: peptide (xi) SEQUENCE DESCRIPTION: SEQ ID NO:19:

Cys  Val  Asp  Lys  Asp  Leu  Gln
1                    5

ANTIBODIES WHICH REACT WITH FIBRINOGEN FRAGMENTS E1, E2 AND E3 AND METHODS OF THEIR USE

The invention relates to peptides, to antibodies produced with their help and to the use of such peptides and antibodies for therapeutic and diagnostic purposes.

The organism is protected from the loss of blood by the coagulation system. The coagulation cascade leads to the activation of the protease thrombin, which converts fibrinogen to fibrin by eliminating the A and B fibrino-peptides. The individual fibrin molecules aggregate to each other (so-called "soft clot") and are then normally crosslinked to each other by the transpeptidase factor XIII (so-called "hard clot"). This wound closure is lysed by the fibrinolytic system, which is activated in a counteractive manner. The key enzyme of fibrinolysis is the protease plasmin, which essentially cleaves fibrinogen and fibrin into the D and E fragments. Fibrinogen is constructed symmetrically from 2 tripeptides, which are linked to each other by means of disulfide bridges in the vicinity of the N termini. When fibrin or fibrinogen is cleaved, 1 molecule of fragment E, which comprises the central linkage region of the fibrin(ogen) molecule, and 2 molecules of fragment D are therefore produced per molecule. In a hard clot, the D domains of the fibrin are crosslinked, so that degradation by plasmin liberates D dimer and fragment E. The E fragment itself is subjected to two further degradation steps. In its first and second form (E1 and E2, respectively), it is bound non-covalently to D dimer and forms the DD/E complex. It is only after the second enzymatic degradation step that the E3 fragment dissociates from the D dimer molecule.

Proteins which carry several immunochemically identical epitopes within one molecule or proteins, such as the D dimer resulting from the cleavage of fibrin or fibrinogen, which, at least under physiological conditions, are constituted as oligomers of protein molecules which in each case carry at least one immunochemically identical epitope, are also designated "intramolecular oligomers".

An unwanted activation of the coagulation system can take place in the vascular system in many pathological situations, resulting in subsequent Occlusion. This can lead to serious heart attacks and thrombo-embolisms. For the purposes of supervising the therapy in patients who are being treated with thrombolytic agents on account of these hypercoagulatory conditions, the success of the lysis must be monitored. This is done by determining the D dimer. However, the thrombolytic agents are not specific, so that fibrinogen can also be degraded to an increased extent as a result of systemic activation of the plasmin. It would be possible to detect this degradation of fibrinogen in a timely manner by determining the E fragment. Fibrinogen is also predominantly degraded in hyperfibrinolytic conditions, triggered, for instance, in sepsis by way of the complement system, which can lead, for example, to the development of disseminated intravascular coagulation (DIC). However, consumption of fibrinogen carries with it an increased risk of bleeding, which risk can thus be recognized diagnostically in a timely manner by determining fragment E, and thereby counteracted therapeutically.

Numerous methods are known for detecting degradation products of fibrin(ogen), such as, for example, the hemaglutination inhibition test (Mersky C. et al., "A rapid, simple, sensitive method for measuring fibrinolytic split products in human serum"; Proc. Soc. Exp. Biol. Med. 131: 871–875 (1969)). This principle was adopted by Schifreen et al., "A quantitative automated immunoassay for fibrinogen/fibrin degradation products", Clin. Chem. 31: 1468–1473 (1985), with the erythrocytes being replaced by latex particles.

Other aggregation assays for determining fibrin(ogen) degradation products utilize latex particles which are coated with antibodies against fibrin(ogen) degradation products. The known antibodies were produced by immunizing with the native degradation products. Antibodies having a variety of specificities were employed.

It is a feature possessed in common by assays which use polyclonal antibodies or fibrinogen receptors that cross-reactivity with fibrinogen exists. As a result of the sample pretreatment which is necessary in the assays, the samples contain different quantities of fibrinogen and artificially produced cleavage products, so that these methods at best permit semiquantitative conclusions (Gaffney P. J. and Perry M. J., "Unreliability of current serum degradation products (FDP) assays", Thromb. Haemost. 53: 301–302 (1985); Nieuwenhuizen W., "Plasma assays of fibrinogen/fibrin degradation products and their clinical relevance", in: Fibrinogen 2, Biochemistry, Physiology and Clinical Relevance. G.D.O. Lowe et al., Edt., 173–180 (1987)).

It is true that, owing to the specificity of the antibodies, assays which use monoclonal antibodies also avoid the problems of cross-reactivity with intact fibrinogen or fibrin. However, for use in agglutination assays, the detected epitope must be available to the antibodies twice on the antigen in order to form aggregates. For this reason, the abovementioned latex assays, for example, which use monoclonal antibodies against D monomer (e.g. Patent Application WO 86/01298), recognize D dimer, which only arises from fibrin following cross-linking, and not D monomer (see Gaffney P. J. et al., "Monoclonal antibodies against fibrinogen, fibrin and their fragments.", Thromb. Haemost. 54:733–734 (1985)). These tests are thus not suitable for detecting fibrin(ogen) degradation products.

In addition to these homogeneous tests, an ELISA has been described recently in which it is possible to differentiate between fibrinogen and fibrin cleavage products with the aid of monoclonal antibodies (Koppert P. W. et al., "A monoclonal antibody-based enzyme immunoassay for fibrin degradation products in plasma", Thromb. Haemostas. 59:310–315 (1988)).

However, as compared with homogeneous methods, the known ELISA methods are, for fundamental reasons, more labor-intensive and more time-consuming and, as a rule, more difficult to automate.

The use of a hexapeptide from the N terminus of the α chain of fibrin, arising under the influence of thrombin, is disclosed in DE 37 01 812.

Hui K. Y. et al. ("Monoclonal antibodies to a synthetic fibrin-like peptide bind to human fibrin but not fibrinogen", Science 222: 1129–1132 (1983)) used a heptapeptide from the corresponding N terminus of the β chain. The antibodies obtained by these methods recognize only fibrin and do not recognize any fibrin(ogen) cleavage products. These assays, and also the detection of the A and B fibrinopeptides which are released during the conversion by thrombin of fibrinogen to fibrin, can be employed for diagnosing hypercoagulatory, but not hyperfibrinolytic, conditions.

Specific antibodies, which react exclusively with fragment E and do not recognize the native fibrinogen or fibrin, are necessary for detecting fibrin(ogen) cleavage products in human blood, synovial fluid or urine. Moreover, these antibodies should be easy to obtain and be usable in all known immunochemical methods, i.e. both heterogeneous and homogeneous test methods.

The present invention was therefore based on the object of making available an antigen which leads to the formation of antibodies against the cleavage products of fibrinogen and fibrin, which antibodies are easy to purify and are specific and thus render possible exact quantification of the fibrinolytic activity in biological fluids, independently of the content of fibrinogen or fibrin. Furthermore, these antibodies should also make possible the use of homogeneous immunoassay techniques in addition to heterogeneous assays.

DETAILED DESCRIPTION OF THE INVENTION

Figure 1:
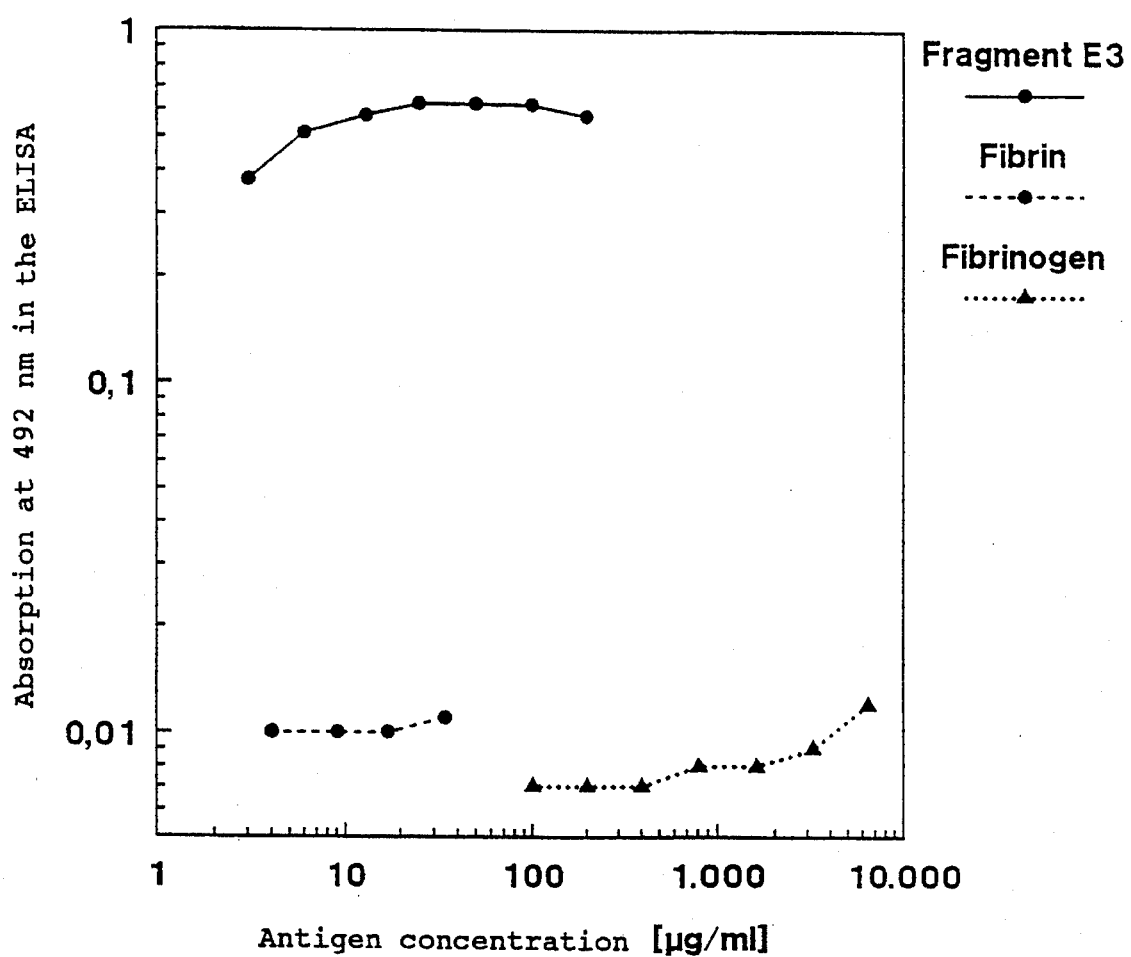
FIGS. 1–5 show the reaction of rabbit antibodies against peptide 3 (SEQ ID NO: 17) with fibrinogen, fibrin and fragment E3 in an ELISA.

It has been found, surprisingly, that, by immunizing animals with synthetic peptides from the C-terminal regions of fragment E, antibodies can be obtained which, while not reacting with fibrinogen or fibrin, react specifically with all 3 E fragments, and, in addition, can be used in agglutination assays.

The invention therefore relates to synthetic peptides which possess amino acid sequences which correspond at least in part to the carboxy terminal ends of the E fragment, which ends arise as a consequence of the cleavage of fibrinogen by plasmin, and are antigenic; preferably, they contain at least one of the following amino acid sequences:

a) Leu-Phe-Glu-Tyr-Gln-Lys-OH, (SEQ ID NO: 1)

b) Tyr-Met-Tyr-Leu-Leu-Lys-OH, (SEQ ID NO: 2)

c) Val-Lys-Glu-Leu-Ile-Lys-OH (SEQ ID NO: 3) and d) His-Gln-Val-Glu-Asn-Lys-OH, (SEQ ID NO: 4)

particularly preferably, at least one of the following amino acid sequences:

a) Asn-Lys-Leu-Lys-Asn-Ser-Leu-Phe-Glu-Tyr-Gln-Lys-OH, (SEQ ID NO: 5)

b) Ser-Ser-Ser-Ser-Phe-Gln-Tyr-Met-Tyr-Leu-Leu-Lys-OH, (SEQ ID NO: 6)

c) Glu-Asn-Lys-Thr-Ser-Gln-Val-Lys-Gln-Leu-Ile-Lys-OH, (SEQ ID NO: 7) and d) Ser-Leu-Glu-Asp-Ile-Leu-His-Gln-Val-Glu-Asn-Lys-OH (SEQ ID NO: 8).

Very particularly preferably, at least one of the following amino acid sequences:

a) His-Gln-Ser-Ala-Cys-Lys-Asp-Ser-Asp-Trp-Pro-Phe-Cys-Ser-Asp-Glu-Asp-Trp-Asn-Tyr-Lys-Cys-Pro-Ser-Gly-Cys-Arg-Met-Lys-Gly-Leu-Ile-Asp-Glu-Val-Asn-Gln-Asp-Phe-Thr-Asn-Arg-Ile-Asn-Lys-Leu-Lys-Asn-Ser-Leu-Phe-Glu-Tyr-Gln-Lys-OH (SEQ ID NO: 9)(peptide 1)

b) Lys-Val-Glu-Arg-Lys-Ala-Pro-Asp-Ala-Gly-Gly-Cys-Leu-His-Ala-Asp-Pro-Asp-Leu-Gly-Val-Leu-Cys-Pro-Thr-Gly-Cys-Gln-Leu-Gln-Glu-Ala-Leu-Leu-Gln-Gln-Glu-Arg-Pro-Ile-Arg-Asn-Ser-Val-Asp-Glu-Leu-Asn-Asn-Asn-Val-Glu-Ala-Val-Ser-Gln-Thr-Ser-Ser-Ser-Ser-Phe-Gln-Tyr-Met-Tyr-Leu-Leu-Lys-OH (SEQ ID NO: 10)(peptide 2)

c) Tyr-Val-Ala-Thr-Arg-Asp-Asn-Cys-Cys-Ile-Leu-Asp-Glu-Arg-Phe-Gly-Ser-Tyr-Cys-Pro-Thr-Thr-Cys-Gly-Ile-Ala-Asp-Phe-Leu-Ser-Thr-Tyr-Gln-Thr-Lys-Val-Asp-Lys-Asp-Leu-Gln-Ser-Leu-Glu-Asp-Ile-Leu-His-Gln-Val-Glu-Asn-Lys-Thr-Ser-Glu-Val-Lys-Gln-Leu-Ile-Lys-OH (SEQ ID NO: 11) (peptide 3) and d) Tyr-Val-Ala-Thr-Arg-Asp-Asn-Cys-Cys-Ile-Leu-Asp-Glu-Arg-Phe-Gly-Ser-Tyr-Cys-Pro-Thr-Thr-Cys-Gly-Ile-Ala-Asp-Phe-Leu-Ser-Thr-Tyr-Gln-Thr-Lys-Val-Asp-Lys-Asp-Leu-Gln-Ser-Leu-Glu-Asp-Ile-Leu-His-Gln-Val-Glu-Asn-Lys (SEQ ID NO: 2) (peptide 4).

Peptides are also preferred which are composed of the amino acid sequences corresponding to peptides 1–3 (SEQ ID NO: 11).

The peptides according to the invention may also be bound to a carrier molecule, either directly or via a spacer.

They are prepared by genetic manipulation or by chemical synthesis.

The invention additionally relates to antibodies which react immunochemically with the peptides according to the invention.

These antibodies are obtained by immunizing an animal with a peptide according to the invention.

Particularly if they are polyclonal, the antibodies according to the invention are preferably isolated and purified by being immunoabsorbed to peptides according to the invention.

The antibodies according to the invention may also preferably be monoclonal antibodies which are prepared by processes known to the person skilled in the art.

The invention also relates to diagnostic methods for the immunochemical determination of intramolecular oligomers of cleavage products of fibrinogen and fibrin, using peptides according to the invention and/or antibodies according to the invention, in particular for determining fibrin(ogen) E fragments and D dimers.

In this context, a heterogeneous immunoassay is preferred, particularly preferably an enzyme immunoassay.

A homogeneous immunoassay is also preferably used, particularly preferably a particle-boosted, nephelometric or turbidimetric test.

In the method, one part of the antibodies is advantageously bound to a solid phase with the other part carrying a detectable function, where a method is preferred which uses microtitration plates as the solid phase and the detectable funtion is a fluorogenic or luminescent dye or an enzyme.

In the homogeneous immunoassay, a particulate, water-in-soluble support is advantageously used as the solid phase and the agglutination reaction is measured nephelometrically or turbidimetrically.

In heterogeneous and homogeneous methods, only one monospecific species is advantageously used, a method also being advantageous, however, in which the capture antibody(ies) is/are an antibody(ies) according to the invention, while the detection antibody(ies) can be different therefrom.

The invention also relates to the use of peptides according to the invention for therapeutic purposes, in particular for the therapy of disturbances of the fibrinolytic system.

The invention further relates to the use of antibodies according to the invention for therapeutic purposes, in particular for the therapy of disturbances of the fibrinolytic system.

In addition to this, the invention relates to an immunochemical method for determining intramolecular oligomers, in which method only one monospecific antibody species is used.

The method may be a heterogeneous assay, preferably an enzyme immunoassay, or a homogeneous immunoassay, preferably a particle-boosted, nephelometric or turbidimetric test.

In the heterogeneous immunoassay, one part of the antibodies is advantageously bound to a solid phase with the other part carrying a detectable function.

In this context, a microtitration plate is preferably used as the solid phase and the detectable function is a fluorogenic or luminescent dye or an enzyme.

Without thereby wishing to stipulate a particular mechanism of action, the assumption appears justified that a lysine at the carboxyterminal end is of importance for the peptides according to the invention.

The peptides according to the invention may be prepared by processes which are known per se to the person skilled in the art, for example (Example 1) protected amino acid derivatives or peptide segments can, in this context, be coupled to each other in solution or on a solid phase, and peptides according to the invention obtained by eliminating the protective groups and, in the case of a solid phase, by cleavage from the carrier resin. In this context, the Fmoc group is preferably used as the temporary protective group, and t-butyl/Boc-based groups for the side groups, the Pmc or Mtr group for Arg, and the tert-butylmercapto or trityl groups for Cys, are preferably used as the permanent protective groups. The C-terminal amino acid is immobilized by way of p-alkoxy-benzyl ester groups which are bound to a polymeric support which is customarily suitable for peptide synthesis, preferably crosslinked polystyrene. The peptide synthesis is effected with the repeated elimination of Fmoc, preferably using 20% piperidine in DMF (dimethyl-formamide) (v/v), and coupling the subsequent, protected amino acid, preferably using a carbodiimide in the presence of HOBT. For this purpose, the amino acid derivative is coupled in an excess, preferably 3-fold, for 1–1.5 h in DMF. After each procedural step, Fmoc elimination or condensation step, the resin is washed 3 times on each occasion with small (15 ml/g) portions of DMF or isopropanol. The peptides according to the invention are cleaved off by acidolysis, with the side chain groups being liberated at the same time. If appropriate, sulfhydryl groups which are to be uncovered are "deproteeted" with tri-n-butylphosphine in an alcohol, for example trifluoroethanol, or with DTT in water. In the case of Cys (TrT) deprotection, a separate procedural step using ethanedithiol as a scavenger is unnecessary. The peptides can be purified, for example, by ion exchange chromatography, reversed-phase chromatography and gel permeation chromatography. The correct composition of the peptides and the peptide contents are determined by amino acid analysis.

Antibodies which are directed against a peptide or polypeptide which corresponds to the region of the γ chain of fibrinogen from amino acid 1 to 62 react specifically with the different forms of the E fragment (see also Example 7). Both the complete polypeptides from the said regions and component sequences of these peptides are suitable for the immunization. A particularly preferred embodiment provides for the use of octadecapeptides, for example having the sequences Val-Asp-Lys-Asp-Leu-Gln-Ser-Leu-Glu-Asp-Ile-Leu-His-Gln-Val-Glu-Asn-Lys(SEQ ID NO: 13) from the C terminus of the γ chain of the E fragment.

For the said cases, it is important that the carboxy terminal sequence of the molecule is exposed and leads to the immunization.

In view of the use planned for the peptides, it is sensible to introduce amino acids possessing reactive side groups into the peptides in such a way that they do not affect the structure of the hapten. For this reason, cysteine, whose free SH group is suitable for coupling via thioether to many carriers, is, where appropriate, expediently added to the N-terminal end. For example, the antigen represented by the abovementioned peptide is preferably made available in the form of the non-adecapeptide Cys-Val-Asp-Lys-Asp-Leu-Gln-Ser-Leu-Glu-Asp-Ile-Leu-His-Gln-Val-Glu-Asn-Lys (SEQ ID NO: 14).

The peptides employed for the immunization can be prepared by chemical synthesis in a manner known per se to the person skilled in the art as well as by purifying a polypeptide prepared by genetic manipulation, or by purifying a peptide which was obtained biochemically from fragment E by the action of proteases and/or chemically by the action of reagents, such as, for example, cyanogen bromide, which cleave peptide chains.

Peptides which are to be employed for the immunization or are to be used as immunoadsorbents are usefully coupled to a carrier molecule. Coupling processes are known per se to the person skilled in the art and are described in the literature (Nakane, P. K. et al., "Peroxidase-Labeled Antibody—A New Method of Conjugation", J. Histochem. Cytochem, 22: 1084–1091 (1974), Freifelder, D. M., "Physical Biochemistry," W. H. Freeman and Co. 1976). Carrier molecules within the meaning of this invention may be: natural or synthetic macromolecules as used by the person skilled in the art for producing an immunoreactive conjugate, for example albumin, ovalbumin, keyhole limpet hemocyanins or polysaccharides. In a preferred embodiment, the peptide or polypeptide is bound to keyhole limpet hemocyanin.

When using the synthetic peptides according to the invention as immunoadsorbents, it is advisable to couple them to materials which are suitable for preparing solid matrices. Carrier molecules in this sense are insoluble polymers as used by the person skilled in the art for immobilizing proteins and peptides, such as, for example, polystyrene, nylon, agarose or magnetizable particles. In this context, the solid phase can be present in any desired form, for example as small tubes, nonwoven fabric, spheres, fibers or microparticles.

A preferred embodiment provides for the coupling of peptides, for example the abovementioned nonadecapeptide, to cyanogen bromide-activated Sepharose.

The immunization of appropriate animals with carrier-bound peptides leads reproducibly to the formation of antibodies. In this context, a preferred animal species for the immunization and isolation of antibodies is the rabbit; in addition to this, mice may also be used for the immunization.

The immunoglobulin fraction which is relevant for specific tests can be enriched by customary immunoadsorptive methods from such an antiserum which has been produced in an animal using synthetic peptides in accordance with the invention. However, in this case, it is preferred likewise to use a peptide which is coupled to a carrier and which possesses the same antigenic determinant as the peptide employed for the immunization as the material for such a matrix employed for the immunoadsorption. The peptide used for the immunoadsorptive purification may also have a truncated amino acid sequence; the sole prerequisite for its use in the immunoadsorptive purification of the desired antibody is that the antigenic determinant formed by this abbreviated polypeptide is recognized and efficiently bound by the desired antibody.

The peptide used for the immunoadsorptive isolation of the antibodies may be, for example, a nonadecapeptide; the peptide Cys-Val-Asp-Lys-Asp-Leu-Gln-Ser-Leu-Glu-Asp-Ile-Leu-His-Gln-Val-Glu-Asn-Lys (SEQ ID NO: 14) is preferred. In accordance with the invention, antibodies are induced in an animal system by immunizing with synthetic peptides and then purified, where appropriate, by immunoadsorption. These antibodies react specifically with the peptides used for the immunization and purification.

By choosing appropriate peptides as immunoadsorbents, antibodies can be selected which preferably react specifically with the antigenic determinant of fragment E which corresponds to the plasmin cleavage site of this molecule. In the preferred case, where peptides possessing sequences from the C-terminal region of the plasmin recognition sequence are used both for the immunization and for the immunoadsorptive purification, antibodies against these sequences are enriched.

Monoclonal antibodies having the properties according to the invention may also advantageously be prepared by processes which are known per se to the person skilled in the art.

The antibodies isolated according to the invention can be employed for homogeneous and heterogenous immunoassays, such as, for example, enzyme immunoassays or free or particle-boosted agglutination reactions, which are known per se to the person skilled in the art. Preferably, they are coupled for this purpose to a solid support. Natural and synthetic, organic and inorganic, polymers, which are known per se to the person skilled in the art, are suitable solid, water-insoluble supports; examples are: polystyrene, polydextrans, polypropylene, polyvinyl chloride, polyvinylidene fluoride, polyacrylamide, agarose, latex, magnetite, porous glass powder, erythrocytes, leucocytes, blood platelets or copolymers consisting of styrene-butadiene, styrene-methacrylic acid or methacrylate-methacrylic acid. Tubes, spheres or microtitration plates are suitable geometric embodiments.

In a preferred manner, the content of fragment E is determined in accordance with the invention by incubating the sample with antibodies which are immobilized on particulate supports, the concentration of fragment E bound by the immobilized antibodies being detected turbidimetrically or nephelometrically by way of the turbidity arising under these circumstances.

In accordance with the invention, the concentration of the D dimer/E complex can also be determined using an antibody immobilized in this way. The prerequisite is the use of a specific antibody against D dimer as a second antibody which is immobilized either on the same or on different particles. One of the two antibodies may also be present free in solution such that immunocomplexes of the configuration: particle-antibody 1/antigen/free antibody 2/antigen/particle antibody 1 are formed and are quantified nephelometrically or turbidimetrically.

In addition, heterogeneous detection methods are preferred in which antibodies according to the invention are immobilized on the solid phase in the ELISA technique. Fragment E or the D dimer/E complex is bound to the immobilized antibody in a first incubation step. The bound antigen is detected in a second incubation step using the same or a different antibody. This second antibody must possess a property which is measurable, for example the ability to convert or bind a chromogenic substrate.

The second antibody can be provided, for example, with an enzyme, a fluorescent molecule, such as, for example, fluorescein isothiocyanate, a radioactive label, or a molecule which is capable of chemiluminescence. Preferably, this second antibody is coupled to a marker enzyme; peroxidase is particularly preferred.

Fragment E or D dimer/E complex can also be determined by simultaneously incubating the sample, preferably of plasma, and labeled antibody together with the immobilized antibodies. In addition to this, a competitive determination method is possible in which labeled and unlabeled fragment E or D dimer/E complex compete for the binding site of the immobilized antibodies. The content of fragment E or D dimer/E complex determined in this way permits conclusions to be drawn with regard to the degree of activation of the fibrinolytic system.

The embodiments specified in the examples are particularly preferred. The examples illustrate the invention without, however, limiting it in any way.

The following abbreviations are used:
ELISA enzyme immunoassay (enzyme linked immunosorbent assay)
KLH keyhole limpet hemocyanin
PBS phosphate-buffered sodium chloride solution (phosphate buffered saline)
Tris tris(hydroxymethyl)aminomethane
OD extinction (optical density)
cysteine Amino acids can be present in the D or L configuration; unless otherwise indicated they are present in the L form.
Val valine
Asp aspartic acid
Lys lysine
Cys cysteine
Leu leucine
Gln glutamine
Ser serine
Glu glutamic acid
Ile isoleucine
His histidine
Asn asparagine
Boc t-butoxycarbonyl
Fmoc 9-fluorenylmethoxycarbonyl
Mtr 4-methoxy-2,3,6-trimethylphenylsulfonyl
DMF dimethylformamide
HOBt hydroxybenzotriazole
DTT dithiothreitol
Trt trityl

EXAMPLE 1

Preparation of an antigen for the immunization a) Synthesis of Cys-Val-Asp-Lys-Asp-Leu-Gln-Ser-Leu-Glu-Asp-Ile-Leu-His-Gln-Val-Glu-Asn-Lys (SEQ ID NO: 14).

1 g of Fmoc-Lys (Boc)-p-alkoxybenzyl ester resin was washed for 1 min 2× with 15 ml of DMF and the Fmoc group was eliminated using 15 ml of 20% piperidine/DMF (v/v) (1×3 min, 1×10 min). The resin was then washed 3× with DMF or isopropanol (15 ml on each occasion) and 2× with 15 ml of DMF. 1.5 mmol of Fmoc amino acid and 2.25 mmol of HOBt dissolved in 15 ml of DMF were added to the resin and, after the addition of 1.65 ml of a 1M diisopropylcarbodiimide solution in dichloromethane, the mixture was shaken at room temperature for 1.5 h. The reaction was examined for completion using a ninhydrin test. The resin was then washed 3× with DMF or isopropanol (15 ml on each occasion), and a new cycle was begun. A Boc-Cys (Trt) was used as the last amino acid. The resin was washed 3× with in each case 15 ml of isopropanol and diethyl ether and dried under high vacuum. 1.9 g of resin were stirred together with 1 ml of thioanisole, 1 ml of ethanedithiol and 18 ml of trifluoroacetic acid at room temperature for 2 h; the mixture was then filtered, with the resin being washed with 3 portions of trifluoroacetic acid/dichloromethane (1:1), and the filtrates were crystallized in ether. The crude peptide was washed with diethyl ether and dried. The peptide was chromatographed on ®Sephadex G 25 in 0.5% acetic acid. Yield: 480 mg. For further purification, 100 mg of this product (=immunization peptide) were chromatographed on a preparative HPLC system on reversed-phase material (0.1% acetonitrile, gradient operation). The peptide pool was freeze dried. Yield: 38 mg.

In accordance with the same process, the following component sequences of the immunizing peptide were prepared for isolating specific antibodies:

Purification peptide 1: Cys-His-Gln-Val-Glu-Asn-Lys (SEQ ID NO: 15)

Purification peptide 2: Cys-Asp-Ile-Leu-His-Gln-Val (SEQ ID NO: 16)

Purification peptide 3: Cys-Ser-Leu-Glu-Asp-Ile-Leu (SEQ ID NO: 17)

Purification peptide 4: Cys-Asp-Leu-Gln-Ser-Leu-Glu (SEQ ID NO: 18)

Purification peptide 5: Cys-Val-Asp-Lys-Asp-Leu-Gln (SEQ ID NO: 19)

b) Conjugate preparation 20 mg of KLH were dissolved in 0.05 M sodium phosphate buffer, pH 8.0, and the mixture was then stirred for 1 hour together with 2 mg of γ-maleimidobutyric acid hydroxysuccinimide ester. The protein was chromatographed on ®Sephadex G 50 (2×30 cm) (0.1M sodium phosphate, 0.5 mM EDTA, pH 6.0). The eluate was concentrated down to 5 ml and incubated for 1 h together with 20 mg of immunizing peptide. Following dialysis and lyophilization, 32 mg of immunizing peptide conjugate were obtained.

EXAMPLE 2

Immunizing rabbits 5 rabbits were immunized with in each case 2.6 mg of antigen per animal over a period of 8 weeks. The peptide-KLH conjugate was administered subcutaneously in the vicinity of lymph nodes. After 3 blood samplings, the animals were exsanguinated and the crude antisera were stabilized with preservative. Yield: about 200 ml of antiserum per animal.

EXAMPLE 3

Preparation of immunoadsorbents

For the purification of the crude antisera by affinity chromatography, 25 mg each of the purification peptides 1 to 5 (SEQ ID NO: 15 to 19), prepared as in Example 1a and encompassing parts of the immunizing peptide, were covalently immobilized on a solid phase. The coupling reaction took place using in each case 5 g of cyanogen bromide-activated Sepharose in accordance with a described process (Axen, R. et al., Nature, 214:1302 (1967)). Subsequently, the immunoadsorbent was in each case washed with phosphate-buffered sodium chloride solution (PBS; 0.15 mol/l, pH 7.2) and acetic acid (0.5 ml/l, pH 2.5). Before use, the adsorbent was equilibrated with a volume of PBS equal to 3 times the gel volume. Yield: in each case about 20 ml of peptide-Sepharose.

EXAMPLE 4

Isolation of specific antibodies

In each case 50 ml of crude antiserum from rabbits, which had been immunized with the immunizing peptide according to Example 2, were loaded onto the PBS-equilibrated 20 ml volumes of peptide-Sepharose from Example 3 (diameter 1.6 cm; height 9 cm) and the columns were subsequently washed with PBS until the extinction at 280 nm was ≦0.01. Washing steps using sodium chloride solution (1 mol/l, pH 7.0) and deionized water (pH 7.0) then took place, with in each case the 3-fold gel volume being used. The antibodies were eluted from the immunoadsorbent with a glycine solution (0.2 mol/l, pH 2.5) and the antibody solution was adjusted to pH 7.0 using a saturated Tris solution, and then dialyzed against PBS. The antibodies were stored until further use at −70° C. The yield depended on the purification peptide (PP) which was used (Table 1).

Table 1: Yield of antibodies from 50 ml of antiserum in relation to the immunizing peptide in accordance with Example 1, following immunoadsorption on component sequences of the immunizing peptide (PP1–PP5)(SEQ ID NO: 15-19).

| PP | Sequence | Yield (mg) |
| --- | --- | --- |
| 1 | Cys—His—Gln—Val—Glu—Asn—Lys (SEQ ID NO: 15) | 6.5 |
| 2 | Cys—Asp—Ile—Leu—His—Gln—Val (SEQ ID NO: 16) | 7.1 |
| 3 | Cys—Ser—Leu—Glu—Asp—Ile—Leu (SEQ ID NO: 17) | 2.3 |
| 4 | Cys—Asp—Leu—Gln—Ser—Leu—Glu (SEQ ID NO: 18) | 1.6 |
| 5 | Cys—Val—Asp—Lys—Asp—Leu—Gln (SEQ ID NO: 19) | 1.2 |

EXAMPLE 5

Preparation of fragment E from fibrinogen and fibrin a) Preparation of fibrin E: Fragments E1 and E2

The different degradation stages of the E fragment (E1, E2 and E3) were prepared in accordance with a described process (Olexa, S. & Budzynski, A. Z., "Binding phenomena of isolated unique plasmic degradation products of human cross-linked fibrin." J. Biol. Chem. 254: 4925–4932 (1979)). 250 mg of test fibrinogen (Behringwerke AG) were dissolved in 100 ml of 0.05 mol/l Tris, 0.1M NaCl (pH 7.8) and induced to clot, at +37° C. by adding 250 units of thrombin and 225 units of F XIII in the presence of 10 mM $CaCl_2$. The fibrin clot was subsequently washed in 0.15 mol/l Tris-HCl (pH 7.4) and then cleaved at +37° C. overnight by adding 1 CTA of plasmin per g of fibrin(ogen) in the presence of 5 mm $CaCl_2$. The reaction was stopped by adding aprotinin (100 KIU per CTA of plasmin) and the cleavage products were separated by gel chromatography on Aca 34 Ultrogel (column diameter 1.7 cm; height 90 cm). The running buffer was 0.05 mol/l Tris, 0.1 mol/l NaCl, 0.028 mol/l Na citrate, 25 KIU/ml antagosan at pH 7.4 Yield: about 100 mg of DD/E complex. The DD/E complex (complex consisting of D dimer together with the E1 and E2 fragments) was subsequently dissociated in 0.05 mol/l citrate, 3M urea at pH 5.5 and +37° C. and the E1 and E2 fragments were separated from D Dimer (ratio of E1 to E2 about 2:1) by rechromatographing on Aca 34 Ultrogel. The running buffer was 0.05 mol/l Tris, 1.0 mol/l NaCl, 0.028 mol/l Na citrate having a pH of 7.4 Yield: about 25 mg of E1/E2 mixture.

b) Preparation of fibrinogen E: fragment E3

250 mg of test fibrinogen (Behringwerke AG) were dissolved in 100 ml of 0.05 mol/l Tris, 0.1M NaCl (pH 7.8) and, after adding 4.7 CTA of plasmin, were cleaved at +37° C. over a period of 30 min in the presence of 5 mM $CaCl_2$. The reaction was stopped by adding aprotinin (20000 KIU). The cleavage products were separated by means of gel chromatography on Aca 34 Ultrogel (column diameter 4 cm; height 90 cm). The running buffer was 0.05 mol/l Tris, 1.0 mol/l NaCl, 0.028 mol/l Na citrate having a pH of 5.7 Yield: about 32 mg of fragment E3.

EXAMPLE 6

Production of soluble fibrin in human plasma 0.6 IU of thrombin were added to 20 ml of a human plasma pool and the mixture was incubated at +37° C. for 90 min. The reaction was stopped by adding 6 ATU of hirudin (from Hoechst AG). The fibrin monomers were determined using the tPA stimulation test (from Kabi, Sweden). Relatively high concentrations of fibrin monomers led to aggregation, and for this reason higher values cannot be expected in the plasma. Yield: 65 µg of fibrin monomers/ml of plasma.

EXAMPLE 7

Use of the antibodies according to the invention in an ELISA a) Preparation of antibody-coated microtitre plates The antibodies isolated in Example 4 were diluted to a concentration of 5 µg/ml with a sodium phosphate solution (0.01 mol/l, pH 5.5) and immobilized by adsorption to microtitre plates (Type B, from Nunc, Denmark). 100 µl of antibody solution per well were incubated at 20° C. for 20 h and the fluid was subsequently sucked off and the plates were washed 3 times with sodium phosphate buffer. 100 µl of a bovine serum albumin solution (0.1 g/l in sodium phosphate 0.01 mol/l, pH 5.5) were then added to each well and the plates were incubated at 20° C. for 1 h. After having been washed 3 times with the sodium phosphate solution, the microtitre plates were stored at +4° C. while being sealed in an airtight manner.

b) Implementation of the enzyme immunoassay

The samples to be tested were diluted 1:2 with incubation buffer (PBS, 0.05% Tween 20, pH 7.2) and in each case 100 µl per well of the coated microtitre plates (in accordance with Example 5a) were incubated at +37° C. for 60 min. Subsequently, the incubation solution was removed and the wells were washed 3× with in each case about 300 µl of washing solution (0.02 mol/l sodium phosphate, 0.05% Tween 20, pH 7.6). Subsequently, 100 µl of peroxidase-conjugated anti-fragment E antibody (from Behringwerke AG, Marburg, FRG) were added and the microtitre plate was incubated at +37° C. for 60 min. After removing the conjugate solution and washing twice, 100 µl of substrate-chromogen solution (hydrogen peroxide, o-phenylenediamine) were added and the microtitre plate was incubated at room temperature. After incubating for 30 minutes, the peroxidase was inactivated with sulfuric acid and the extinction of the reaction solution was determined at 490 nm.

EXAMPLE 8

Investigation of the antibodies purified by immunoadsorption a) Reaction with fibrinogen, fibrin and fragment E3

To investigate the specificity of the antibodies, isolated in accordance with Example 4 using the purification peptides 1 to 5 (SEQ ID NO: 15 to 19) (PP1–PP5), a comparative investigation was carried out by ELISA in accordance with Example 7 of their reactivity with fibrinogen, fibrin (the degradation product of fibrinogen by the action of thrombin) and with fragment E3 (the degradation product of fibrinogen by the action of plasmin). The following were used: fibrin monomer produced in plasma in accordance with Example 6 and having a concentration of 34 µg/ml, as the fibrin source, E3 produced in accordance with Example 5b) and having a concentration of 200 µg/ml, as fragment E3, and test fibrinogen (from Behringwerke AG) having a concentration of 6400 µg/ml. The samples were diluted serially 1:2 in incubation buffer (Example 7).

It is evident from these results (see Table 2 and FIGS. 1 to 5) that the antibodies prepared according to the invention react very strongly with the fibrinogen cleavage product resulting from the action of plasmin. The antibodies purified by immunoadsorption using PP1 (SEQ ID NO: 15) or PP5 (SEQ ID NO: 19) do not exhibit any cross reaction with fibrin monomer or fibrinogen. Purification of antibodies using PP2 (SEQ ID NO: 16), PP3 (SEQ ID NO: 17) and PP4 (SEQ ID NO:18) also gives rise to antibodies which either do not react with fibrin monomers or only react to a negligible extent. In the case of the antibodies isolated using PP3 (SEQ ID NO: 17), their reaction with fibrinogen may likewise be disregarded. Consequently, this process is suitable for obtaining specific antibodies which do not require any further "final purification".

Table 2: Reaction of the antibodies, isolated in accordance with the invention, against component sequences of the immunizing peptide with fibrinogen and with the cleavage products resulting from thrombin digestion (fibrin monomers) or plasmin digestion (fragment E3) in buffer in the ELISA. The measurement values in the ELISA are given; antigen concentrations in µg/ml. Purification peptides 1 through 5 in Table 2 are represented by SEQ ID NOS: 15 through 19, respectively.

TABLE 2

| PP | Fibrinogen | | Fragment E3 | | Fibrin | |
|---|---|---|---|---|---|---|
|  | Conc. | Ext. | Conc. | Ext. | Conc. | Ext. |
| 1 | 0 | 0.007 | 0 | 0.007 |  |  |
|  | 100 | 0.007 | 3 | 0.377 | 4 | 0.010 |
|  | 200 | 0.007 | 6 | 0.512 | 9 | 0.010 |
|  | 400 | 0.007 | 13 | 0.576 | 17 | 0.010 |
|  | 800 | 0.008 | 25 | 0.624 | 34 | 0.011 |
|  | 1600 | 0.008 | 50 | 0.624 |  |  |
|  | 3200 | 0.009 | 100 | 0.620 |  |  |
|  | 6400 | 0.012 | 200 | 0.574 |  |  |
| 2 | 0 | 0.007 | 0 | 0.007 |  |  |
|  | 100 | 0.008 | 3 | 0.021 | 4 | 0.010 |
|  | 200 | 0.008 | 6 | 0.036 | 9 | 0.009 |
|  | 400 | 0.010 | 13 | 0.060 | 17 | 0.010 |
|  | 800 | 0.015 | 25 | 0.107 | 34 | 0.010 |
|  | 1600 | 0.019 | 50 | 0.167 |  |  |
|  | 3200 | 0.029 | 100 | 0.243 |  |  |
|  | 6400 | 0.037 | 200 | 0.325 |  |  |
| 3 | 0 | 0.007 | 0 | 0.011 |  |  |
|  | 100 | 0.009 | 3 | 0.064 | 4 | 0.013 |
|  | 200 | 0.012 | 6 | 0.109 | 9 | 0.013 |
|  | 400 | 0.015 | 13 | 0.176 | 17 | 0.013 |
|  | 800 | 0.023 | 25 | 0.282 | 34 | 0.013 |
|  | 1600 | 0.034 | 50 | 0.375 |  |  |
|  | 3200 | 0.040 | 100 | 0.464 |  |  |
|  | 6400 | 0.065 | 200 | 0.529 |  |  |
| 4 | 0 | 0.007 | 0 | 0.007 |  |  |
|  | 100 | 0.009 | 3 | 0.032 | 4 | 0.015 |
|  | 200 | 0.011 | 6 | 0.055 | 9 | 0.016 |
|  | 400 | 0.016 | 13 | 0.113 | 17 | 0.020 |
|  | 800 | 0.030 | 25 | 0.207 | 34 | 0.032 |
|  | 1600 | 0.043 | 50 | 0.349 |  |  |
|  | 3200 | 0.060 | 100 | 0.558 |  |  |
|  | 6400 | 0.052 | 200 | 0.781 |  |  |
| 5 | 0 | 0.008 | 0 | 0.007 |  |  |
|  | 100 | 0.007 | 3 | 0.015 | 4 | 0.009 |
|  | 200 | 0.007 | 6 | 0.026 | 9 | 0.009 |
|  | 400 | 0.008 | 13 | 0.045 | 17 | 0.009 |

TABLE 2-continued

| PP | Fibrinogen Conc. | Ext. | Fragment E3 Conc. | Ext. | Fibrin Conc. | Ext. |
|---|---|---|---|---|---|---|
|  | 800 | 0.008 | 25 | 0.084 | 34 | 0.011 |
|  | 1600 | 0.007 | 50 | 0.124 |  |  |
|  | 3200 | 0.007 | 100 | 0.165 |  |  |
|  | 6400 | 0.008 | 200 | 0.191 |  |  | b) Reaction with different E fragments

In analogy with Example 8a), a comparative investigation was carried out of the reactivity of the antibodies, purified immunoadsorptively using the different component sequences of the immunizing peptide, with fragment E from crosslinked fibrin (fragment mixture E1/E2; prepared in accordance with Example 5a) and from fibrinogen (fragment E3; prepared in accordance with Example 5b). The concentration of the stock solutions was 2 µg/ml.

It is evident from Table 3 (see also FIGS. 6–10) that all the antibodies prepared according to the invention react equally well both with fragment E3 and with the E1/E2 fragment mixture. On the other hand, antibodies purified using PP4 (SEQ ID NO: 18) and PP5 (SEQ ID NO: 19) discriminate between fragment E from fibrinogen and E from crosslinked fibrin. In this example, the limit of detection was in the region of 1 ng/ml. The antibodies according to the invention are thus suitable for the sensitive diagnosis of both primary and secondary fibrinolysis.

Table 3: Reaction of the antibodies, isolated in accordance with the invention, against component sequences of the immunizing peptide with fragment E (E3) from fibrinogen (primary fibrinolysis) and with fragment E (E1/E2) from crosslinked fibrin (secondary fibrinolysis) in buffer in the ELISA. The measurement values in the ELISA are given; antigen concentrations in ng/ml. Purification peptides 1 through 5 in Table 3 are represented by SEQ ID NOS: 15 through 19, respectively.

TABLE 3

| Fragments conc. | E1/E2 ext. | E3 ext. | E1/E2 ext. | E3 ext. | E1/E2 ext. | E3 ext. |
|---|---|---|---|---|---|---|
|  |  |  | Purification peptide |  |  |  |
|  | PP1 |  | PP2 |  | PP3 |  |
| 0 | 0.079 | 0.079 | 0.014 | 0.014 | 0.017 | 0.017 |
| 1 | 0.557 | 0.249 | 0.048 | 0.024 | 0.113 | 0.041 |
| 2 | 0.622 | 0.336 | 0.072 | 0.032 | 0.182 | 0.060 |
| 4 | 0.707 | 0.329 | 0.115 | 0.045 | 0.230 | 0.113 |
| 8 | 1.126 | 0.530 | 0.191 | 0.075 | 0.459 | 0.162 |
| 16 | 1.628 | 0.804 | 0.236 | 0.112 | 0.636 | 0.240 |
| 31 | 1.975 | 1.243 | 0.438 | 0.185 | 1.005 | 0.434 |
| 63 | 2.061 | 1.672 | 0.623 | 0.275 | 1.272 | 0.604 |
| 125 | 2.230 | 2.044 | 0.765 | 0.512 | 1.581 | 0.988 |
| 250 | 2.145 | 2.023 | 1.059 | 0.742 | 1.818 | 1.392 |
| 500 | 2.287 | 2.127 | 1.283 | 1.077 | 1.931 | 1.812 |
| 1000 | 2.264 | 2.232 | 1.426 | 1.580 | 1.593 | 2.118 |
| 2000 | 2.272 | 2.145 | 1.568 | 1.945 | 1.990 | 2.445 |
|  |  | Purification peptide |  |  |  |  |
|  | PP4 |  | PP5 |  |  |  |
| 0 | 0.019 | 0.019 | 0.022 | 0.022 |  |  |
| 1 | 0.082 | 0.043 | 0.049 | 0.028 |  |  |
| 2 | 0.140 | 0.036 | 0.075 | 0.033 |  |  |
| 4 | 0.236 | 0.050 | 0.118 | 0.042 |  |  |
| 8 | 0.361 | 0.074 | 0.195 | 0.058 |  |  |
| 16 | 0.698 | 0.138 | 0.371 | 0.112 |  |  |
| 31 | 1.033 | 0.265 | 0.603 | 0.189 |  |  |
| 633 | 1.400 | 0.422 | 0.863 | 0.327 |  |  |
| 125 | 1.853 | 0.718 | 1.185 | 0.537 |  |  |

TABLE 3-continued

| Fragments conc. | E1/E2 ext. | E3 ext. | E1/E2 ext. | E3 ext. | E1/E2 ext. | E3 ext. |
|---|---|---|---|---|---|---|
| 250 | 2.096 | 1.086 | 1.567 | 0.790 |  |  |
| 500 | 2.374 | 1.585 | 1.780 | 1.083 |  |  |
| 1000 | 2.688 | 2.242 | 2.019 | 1.389 |  |  |
| 2000 | 3.000 | 2.745 | 2.046 | 1.597 |  |  | c) Reaction with fragment E in buffer and plasma

To examine whether the antibodies, purified according to the invention (see Example 4), are also suitable for detecting fibrin(ogen) degradation products in plasma, a comparative investigation was made, in analogy with Example 8a), of the reactivity of the purified antibodies with fragment E from fibrinogen (fragment E3; prepared in accordance with Example 5b) in the buffer system and following the addition of a human plasma pool containing purified fragment E3. The concentration of the stock solutions was 200 µg/ml.

It is evident from Table 4 (see also FIGS. 11–13) that fibrin(ogen) degradation products can also be detected in the presence of native fibrinogen in plasma. Owing to the different matrix, the measurement signals in the plasma are only slightly lower.

Table 4: Reaction of the antibodies, isolated in accordance with the invention, against component sequences of the immunizing peptide (PP1 (SEQ ID NO: 15) to PP3(SEQ ID NO: 1)) with fragment E (E3) in buffer and plasma in the ELISA. The measurement values in the ELISA are given; antigen concentrations in µg/ml. Purification peptides 1 through 5 in Table 4 are represented by SEQ ID NOS: 15 through 19, respectively.

TABLE 4

| | Purification peptide | | | | | |
|---|---|---|---|---|---|---|
| | PP1 | | PP2 | | PP3 | |
| E3 conc. | Buffer ext. | Plasma ext. | Buffer ext. | Plasma ext. | Buffer ext. | Plasma ext. |
| 0 | 0.007 | 0.008 | 0.007 | 0.010 | 0.011 | 0.011 |
| 3 | 0.377 | 0.273 | 0.021 | 0.018 | 0.064 | 0.047 |
| 6 | 0.512 | 0.414 | 0.036 | 0.027 | 0.109 | 0.075 |
| 13 | 0.576 | 0.525 | 0.060 | 0.049 | 0.176 | 0.132 |
| 25 | 0.624 | 0.581 | 0.107 | 0.075 | 0.282 | 0.190 |
| 50 | 0.624 | 0.588 | 0.167 | 0.120 | 0.375 | 0.270 |
| 100 | 0.620 | 0.588 | 0.243 | 0.191 | 0.464 | 0.342 |
| 200 | 0.574 | 0.580 | 0.325 | 0.279 | 0.529 | 0.435 | d) Reaction with fibrin degradation products produced in vitro

30 ATU of hirudin (from Hoechst AG) were in each case added to 3 ml of a human plasma pool and 3 ml of a plasma deficient in α2-antiplasmin and the samples were subsequently incubated at +37° C. together with plasmin (final concentration 1 CTA/ml). After 0, 1, 2, 5, 10, 30 and 60 min, 60 µl of antagosan solution (from Behringwerke AG; 100 APE/ml) were in each case added to 600 µl of the plasmas and the appearance of fibrinogen degradation products was followed, in accordance with Example 7, in the ELISA using the different purified antibodies from Example 4.

The measurement values in the ELISA, listed in Table 5 (see FIGS. 14–16), show that the fibrinogen degradation products produced in vitro by adding plasmin to the plasma deficient in α2-antiplasmin can be detected on solid phase using the antibodies isolated against the purification peptides PP1 to PP3 (SEQ ID NO: 15 to 17). On the other hand, the added plasmin is inhibited by α2-antiplasmin in the plasma pool from normal blood donors and no fibrinogen cleavage products arise. Correspondingly, no measurement signal can be noted in the ELISA which is higher than that at time point 0.

Table 5: Time course for the appearance of fibrinogen degradation products during treatment of normal plasma (SHP) and of a plasma deficient in α2-antiplasmin (α2-DP) with plasmin. The listed values are the measurement values obtained when determining the fibrinogen degradation products in the ELISA according to Example 7 using the antibodies on the solid phase which were purified against the component sequences PP1, PP2 or PP3 of the immunizing peptide. Purification peptides 1 through 3 in Table 3 are represented by SEQ ID NOS: 15 through 17, respectively.

TABLE 5

| | Purification peptide | | | | | |
|---|---|---|---|---|---|---|
| | PP1 | | PP2 | | PP3 | |
| Time min | SHP ext. | α2-MP ext. | SHP ext. | α2-MP ext. | SHP ext. | α-MP ext. |
| 0 | 0.056 | 0.024 | 0.073 | 0.066 | 0.081 | 0.076 |
| 1 | 0.015 | 0.084 | 0.043 | 0.096 | 0.043 | 0.111 |
| 2 | 0.018 | 0.218 | 0.042 | 0.124 | 0.047 | 0.179 |
| 5 | 0.022 | 0.654 | 0.039 | 0.159 | 0.049 | 0.364 |
| 10 | 0.021 | 1.153 | 0.042 | 0.279 | 0.052 | 0.669 |
| 30 | 0.022 | 1.336 | 0.043 | 0.402 | 0.056 | 0.880 |
| 60 | 0.023 | 1.333 | 0.052 | 0.397 | 0.060 | 0.822 |

EXAMPLE 9

Use of the antibodies according to the invention in an agglutination test.

a) Preparation of a latex reagent for determining fibrin(ogen) degradation products.

Latex reagents were prepared by the method of Kapmeyer W. H. et al. "Automated nephelometric immunoassays with novel shell/core particles." J. Clin. Lab. Anal. 2:76–83 (1988). 1 ml of a graft polymer (4% strength solution; from Behringwerke AG) was mixed with 0.1 ml of an antibody solution (purified according to Example 4; concentration: 0.4 mg/ml; corresponds to a coupling ratio of 1:100) and 0.05 ml of a 20% strength aqueous solution of Tween® 20. To activate the latex, the solution was adjusted to a pH of 2 using about 0.01 ml of a 1N HCl solution. After a 30 minute incubation at room temperature, 0.25 ml of a saturated sodium hydrogen phosphate solution (pH 6.5) and 0.25 ml of an aqueous solution of sodium cyanoborohydride (25 mg/ml) were added and the reagents were thoroughly mixed. Coupling of the antibody to the activated aldehyde groups took place at room temperature over a period of 1 h. Subsequently, the latex-antibody conjugate was centrifuged (Beckman centrifuge, 40000×g, 30 min) and the pellet was then resuspended in 1.5 ml of a 0.1 molar glycine buffer (pH 8.2; containing 0.17M NaCl and 0.5% Tween® 20). The solution was then ultrasonicated for about 5 s (Bronson Sonifier B 15). This stock solution was stored at +4° C.

b) Implementation of nephelometric determinations

The reaction of the anti-fibrin(ogen) degradation product latices (anti-FDP latex) with the fibrin(ogen) degradation products was followed on a BNA nephelometer from Behringwerke AG, Marburg. The stock solutions prepared as described under Example 9b) were diluted with physiological sodium chloride solution to a concentration of 0.03%. 50 µl of this suspension were mixed with 20 µl of D dimer (from Behringwerke AG), as a supplementary reagent, and 80 µl of N diluent (from Behringwerke AG). Following the addition of 50 µl of sample and 70 µl of N diluent, the increase in turbidity was measured after incubating for 12 minutes.

c) Reaction of the antibody-coated latex particles with fibrin(ogen) degradation products Antibodies isolated against purification peptide PP1 (SEQ ID NO: 15) in accordance with Example 4 were bound to latex particles having a diameter of 230 nm using the process described under Example 9a). The reaction of the anti-FOP latex with the fibrinogen degradation product E3 and the fibrin degradation products E1/E2 was followed in accordance with Example 9b). The antigens were present in physiological sodium chloride solution and were appropriately diluted, prior to measurement, by the equipment from a 2.5-fold concentrated stock solution.

The measurement signals listed in Table 6 show an increase in turbidity which is dependent on the concentration of the fibrin(ogen) degradation products. This agglutination reaction consequently proves the suitability of the antibodies according to the invention for detecting fibrin(ogen) degradation products in accordance with the hypothesis of an "internal dimer" in the different E fragments.

Table 6: Increase in turbidity during the reaction of anti-FDP latex with the degradation products of fibrin and fibrinogen. The measured differences in turbidity (in bit) are listed which were obtained on a nephelometer CBNA; Behringwerke AG) following a 12-minute incubation of an anti-FDP latex suspension with degradation products of either fibrin (E1/E2) or fibrinogen (E3). The concentration of the antigens is given in mg/l.

TABLE 6

| Fragment conc. | E1/E2 ext. | E3 ext. |
|---|---|---|
| 1.3 | 602 | 414 |
| 2.5 | 876 | 459 |
| 5.0 | 1001 | 558 |
| 10.0 | 1288 | 699 |
| 20.0 | 1473 | 886 |

Legend to the figures:
FIGS. 1–5:
Reaction of rabbit antibodies against peptide 3 (SEQ ID NO: 17) with fibrinogen, fibrin and fragment E3 in the ELISA.

Antibodies were produced in rabbits by immunizing with a peptide from the carboxy-terminal region of the γ-chain of fragment E (peptide 3). The antibodies were purified by immunoadsorption to solid phase-immobilized hexapeptides whose sequences corresponded in part to that of the immunizing peptide (purification peptides PP1 to PP5)(SEQ ID NO: 15 to 19). These antibodies were used for coating microtitration plates and their reaction with fibrinogen, fibrin and fragment E3 from plasmin-degraded fibrinogen was tested in a sandwich ELISA. A conjugate consisting of unspecific antibodies against fragment E and horseradish peroxidase was used for detecting the bound antigen. The signals shown are those measured in the ELISA when using fibrinogen and fragment E3 in sample buffer or using fibrin-containing plasma.

FIG. 1: antibody purified against PP1 (SEQ ID NO: 15).

Figure 2:
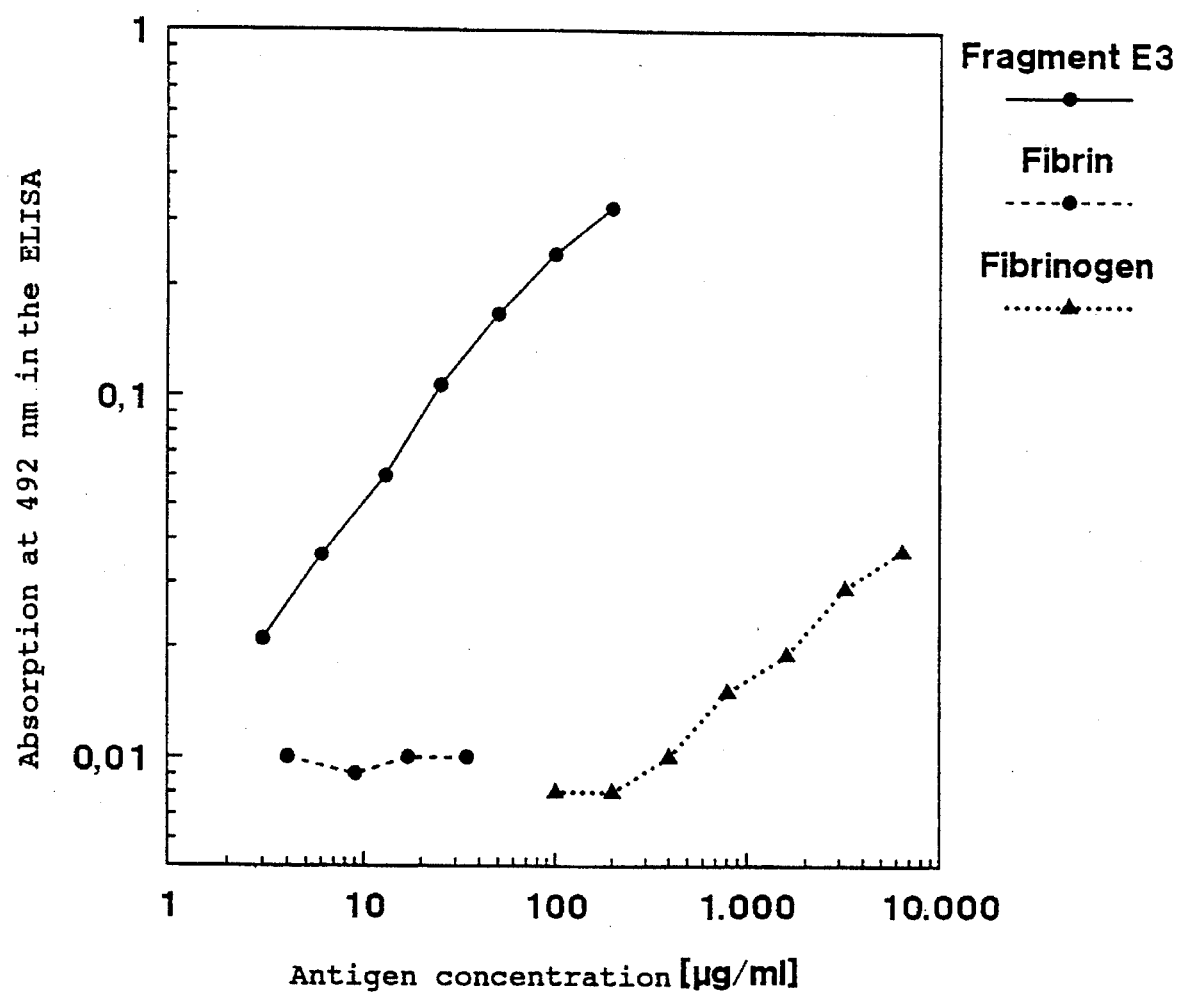

FIG. 2: antibody purified against PP2 (SEQ ID NO: 16).

Figure 3:
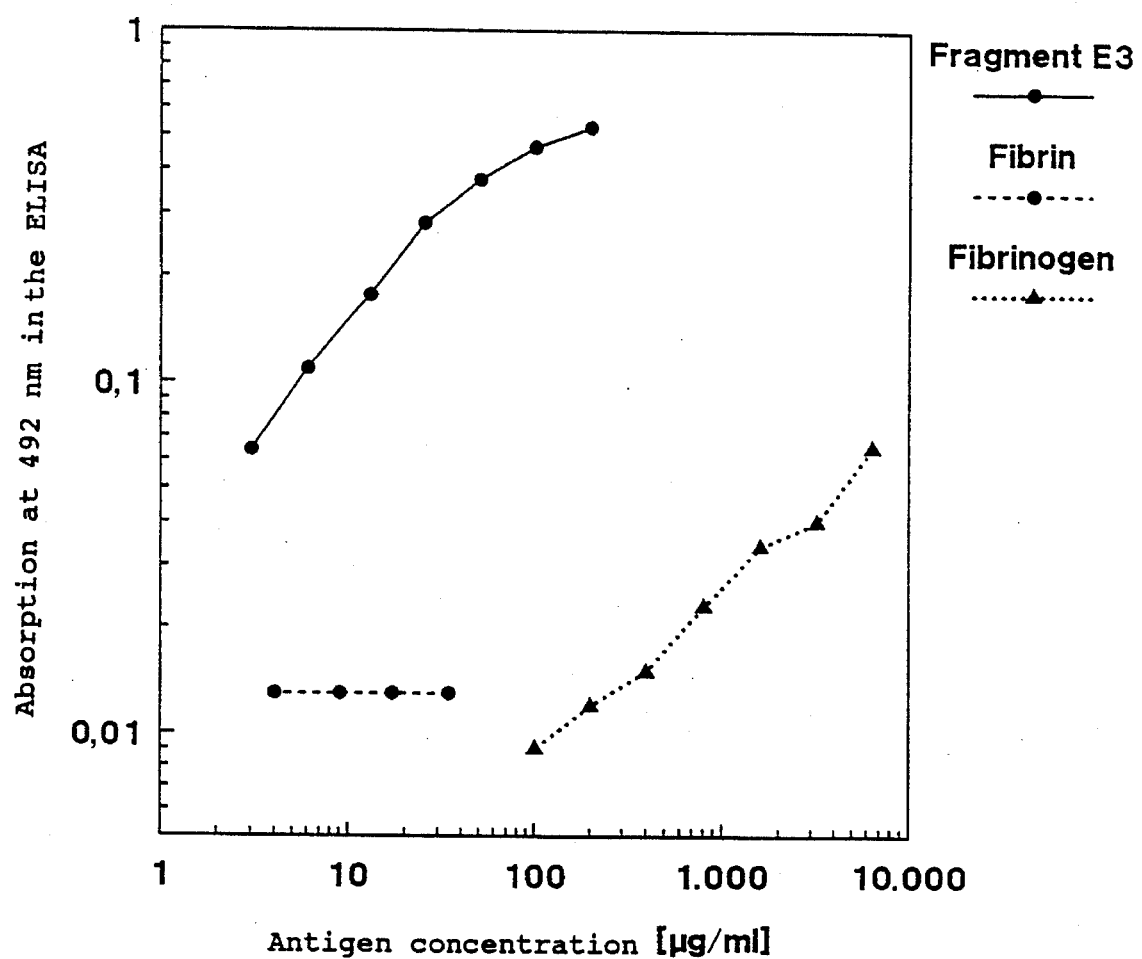

FIG. 3: antibody purified against PP3 (SEQ ID NO: 17).

Figure 4:
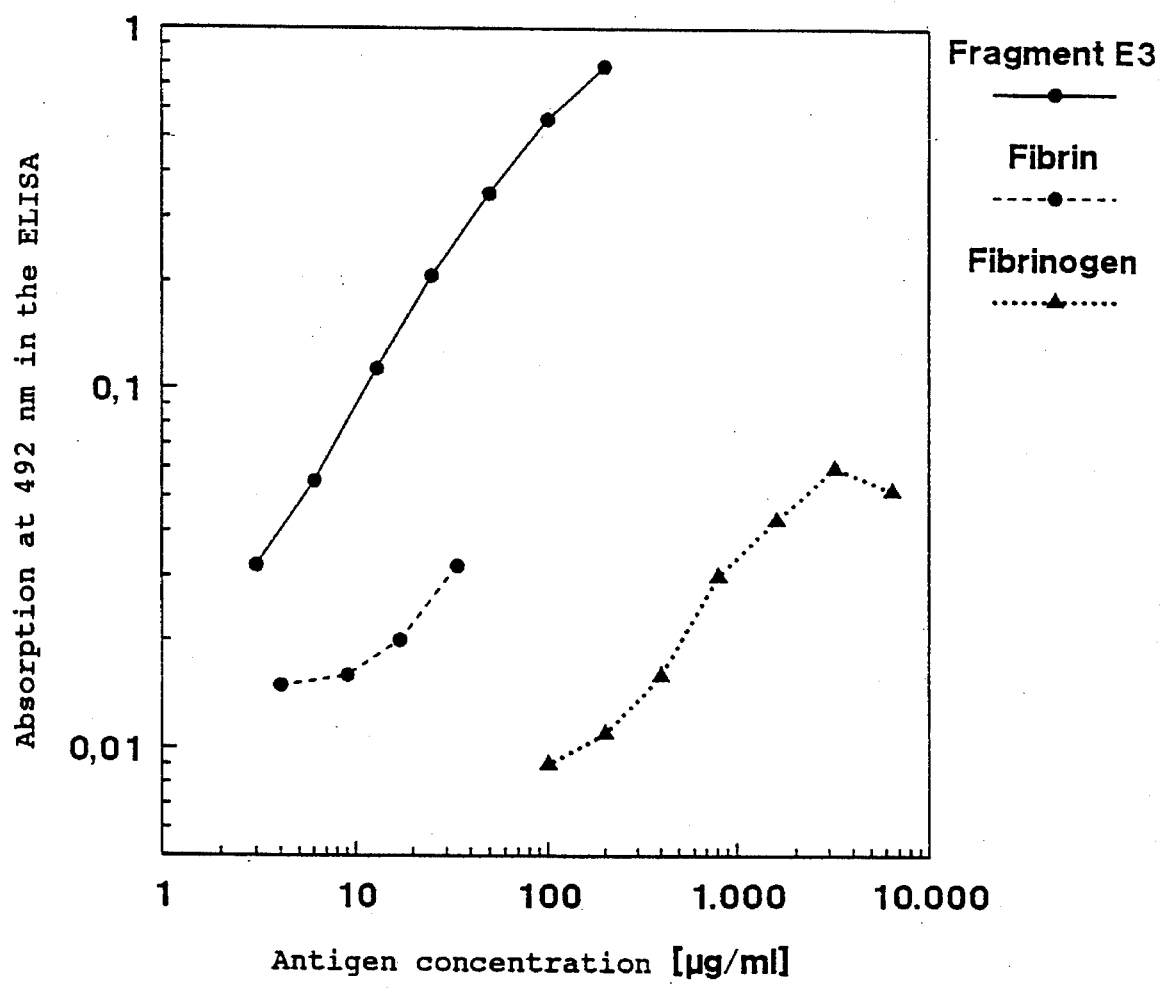

FIG. 4: antibody purified against PP4 (SEQ ID NO: 18).

Figure 5:
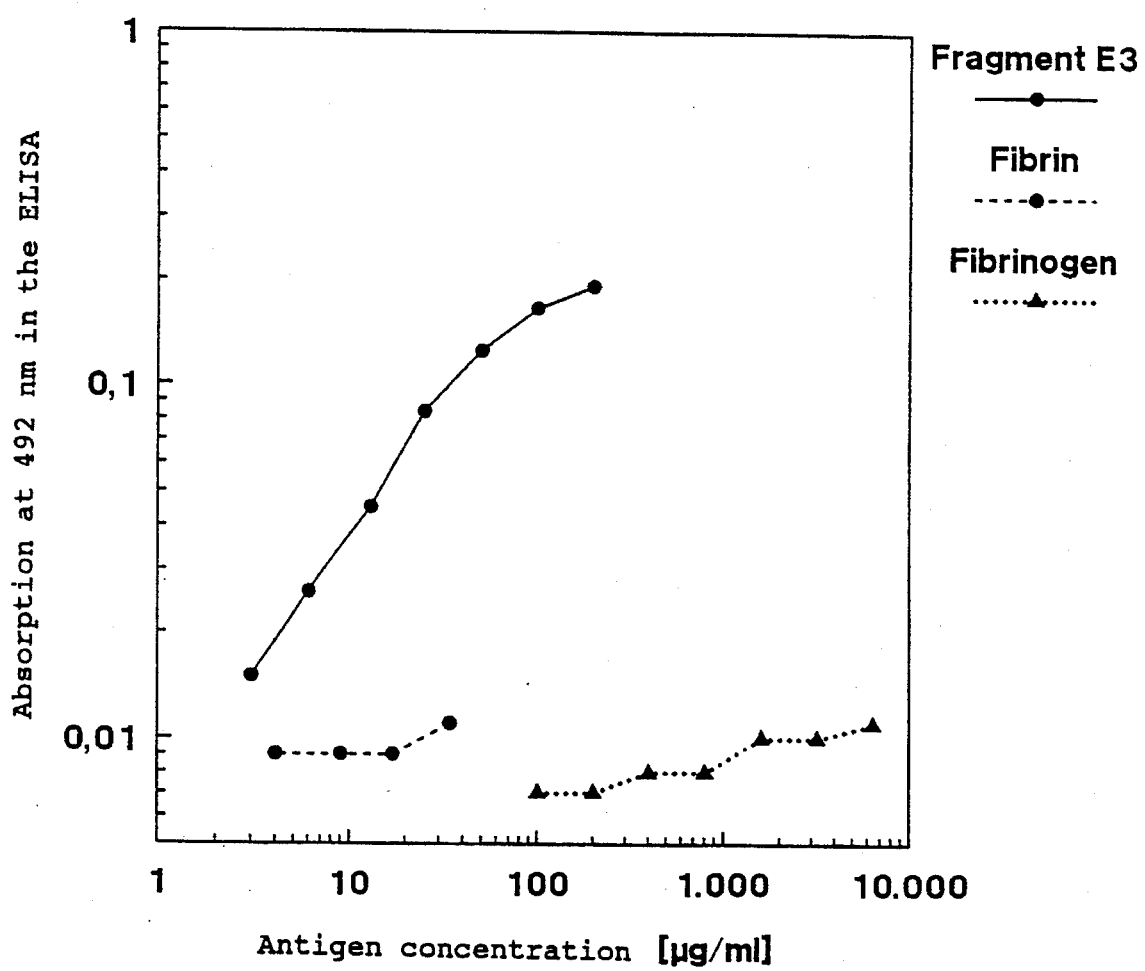

FIG. 5: antibody purified against PP5 (SEQ ID NO: 19).

FIGS. 6–10:
Reaction of rabbit antibodies against peptide 3 (SEQ ID NO: 17) with fragment E from fibrinogen (E3) and from fibrin (E1/E2) in the ELISA.

A mixture of fragments E1 and E2, which were isolated from the D dimer/E complex following the action of plasmin on crosslinked fibrin, and fragment E3, which was purified following the action of plasmin on fibrinogen, were employed as antigens in the ELISA. The same antibodies were used as described in the legend to FIGS. 1–5. The signals shown are those measured in the ELISA when using fragment E1/E2 and fragment E3, as well as the background signal obtained when using sample buffer as the sample.

Figure 6:
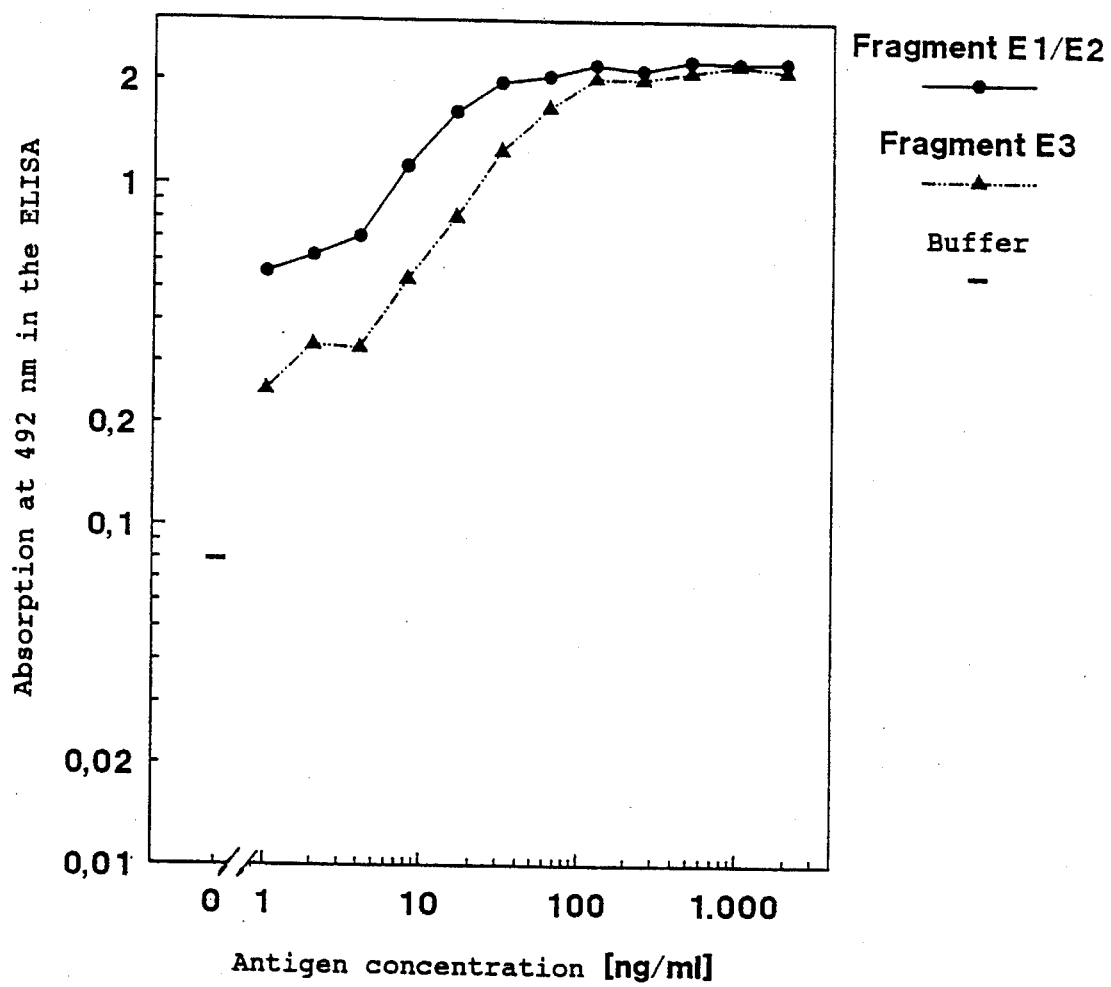
FIGS. 6–10 show the reaction of rabbit antibodies against peptide 3 (SEQ ID NO: 17) with fragment E from fibrinogen (E3) and from fibrin (E1/E2) in an ELISA.
Figure 7:
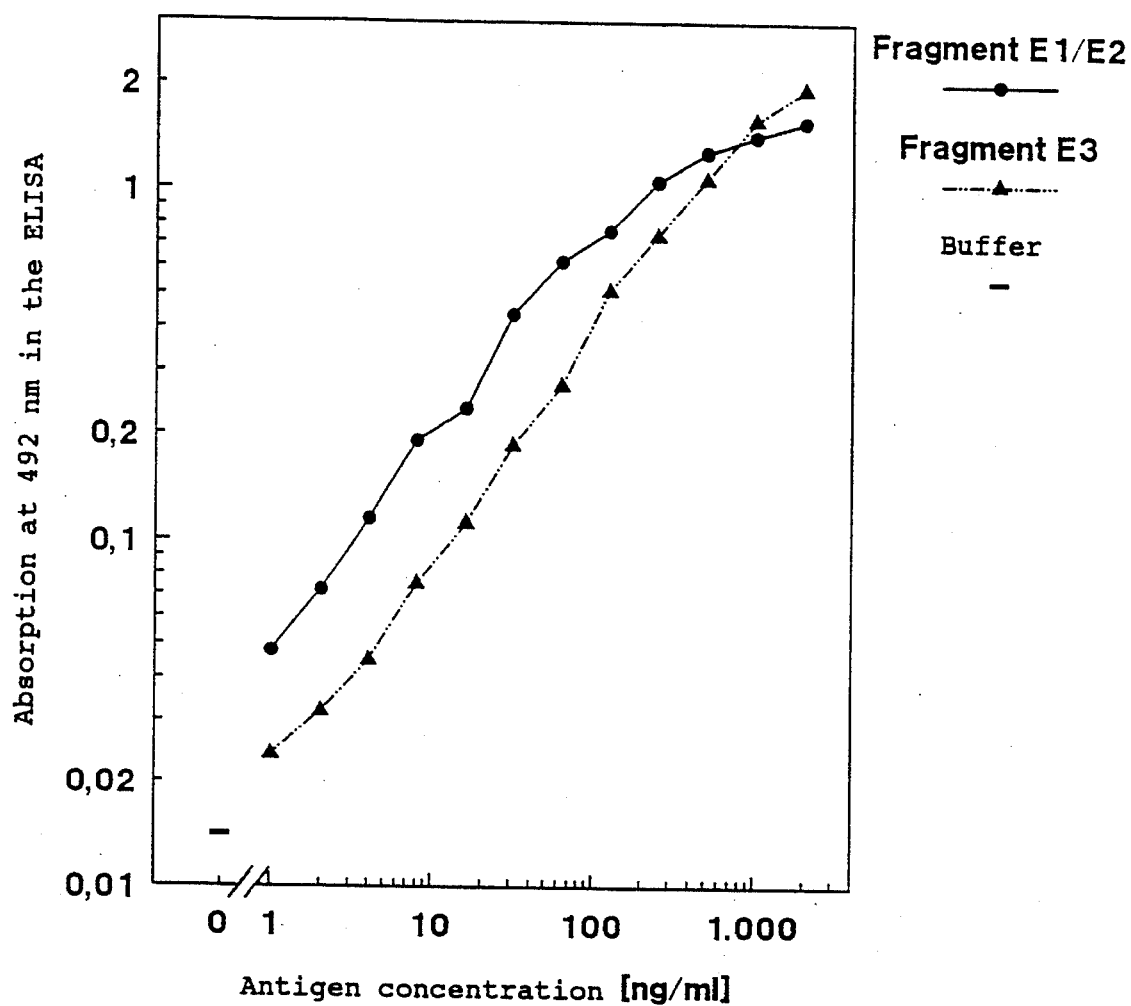
Figure 8:
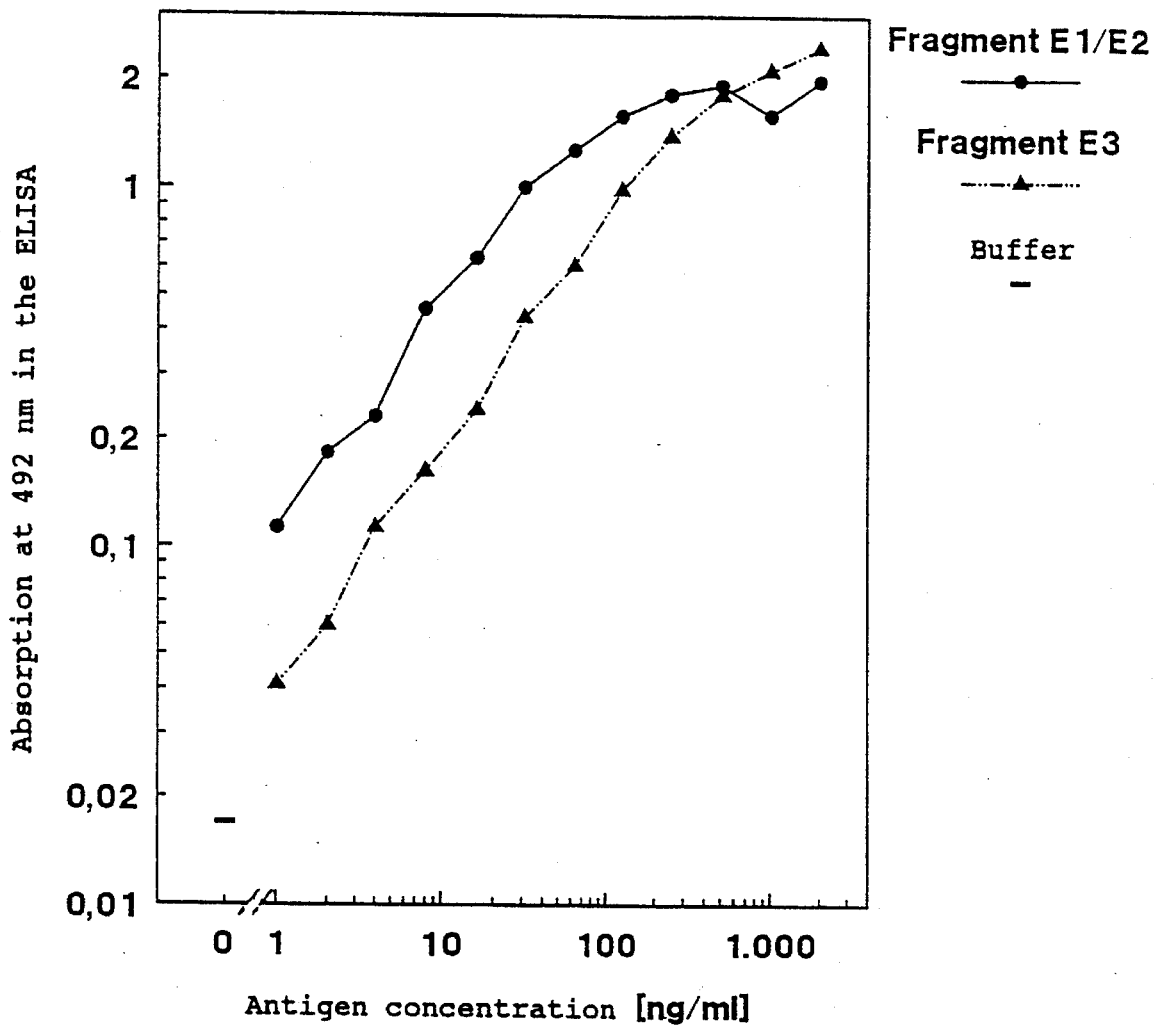
Figure 9:
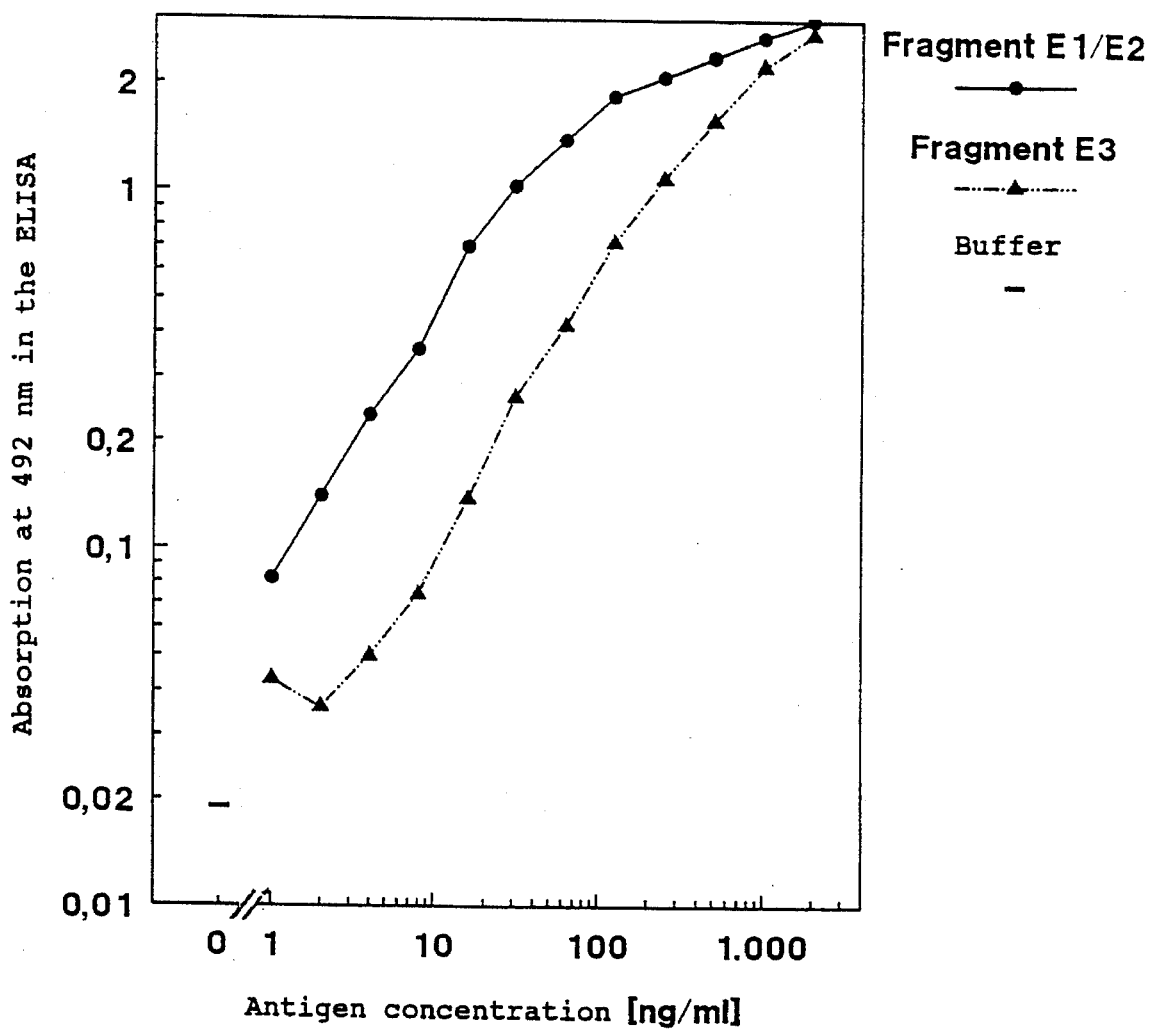
Figure 10:
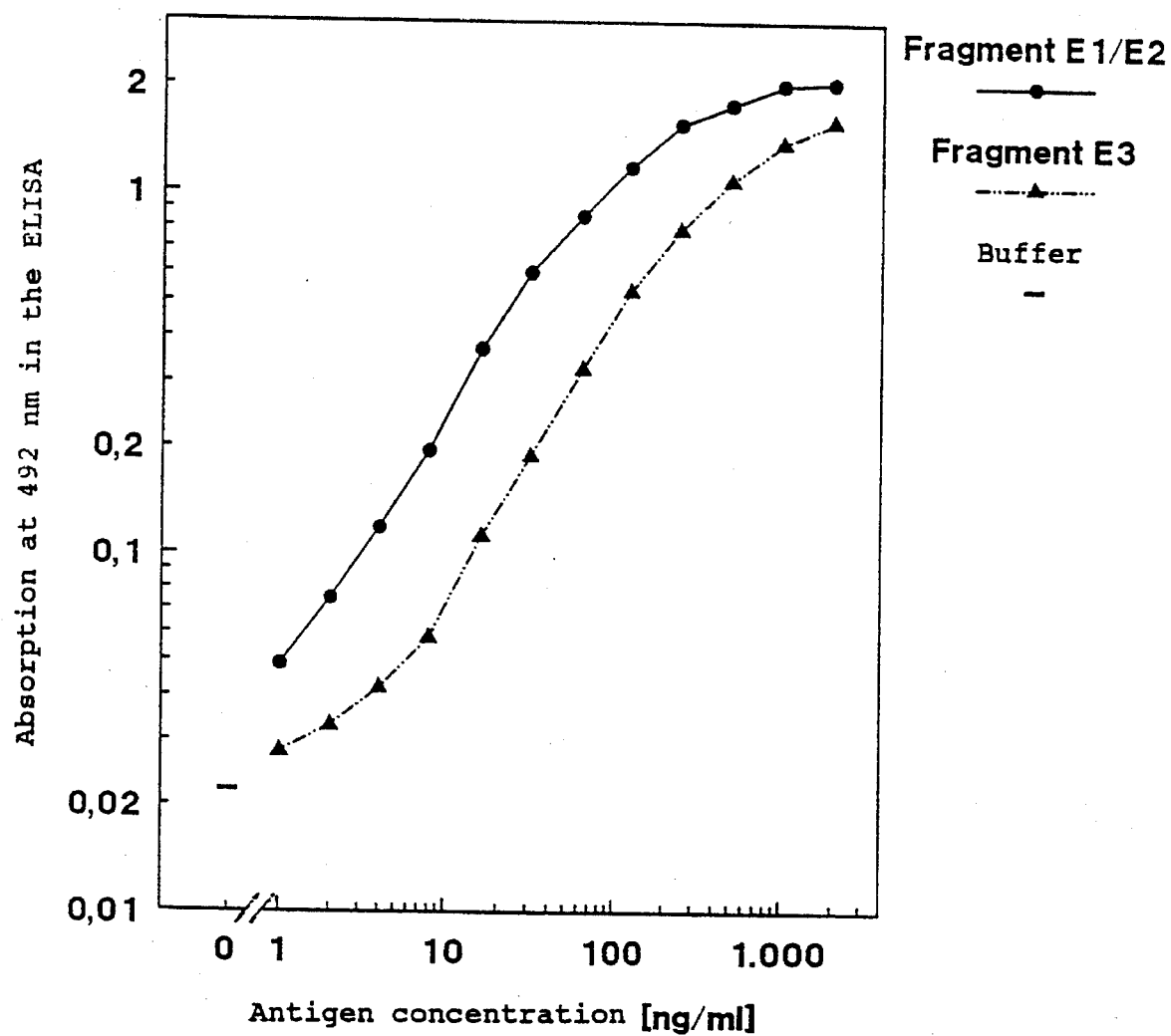

FIG. 6: antibody purified against PP1 (SEQ ID NO: 15).
FIG. 7: antibody purified against PP2 (SEQ ID NO: 16).
FIG. 8: antibody purified against PP3 (SEQ ID NO: 17).
FIG. 9: antibody purified against PP4 (SEQ ID NO: 18).
FIG. 10: antibody purified against PP5 (SEQ ID NO: 19).

FIGS. 11–13:

Reaction of rabbit antibodies against peptide 3 (SEQ ID NO: 17) with fragment E from fibrinogen (E3) in sample buffer and in human plasma in the ELISA.

Fragment E, which was prepared by the action of plasmin on fibrinogen (=fragment E3), was diluted to various concentrations in buffer medium or in human plasma and its reaction with the antibodies described in the legend to FIGS. 1–5 was followed in the ELISA. The signals shown are those measured in the ELISA using the antigen, as well as the background signal obtained when using buffer or plasma which was free of antigen.

Figure 11:
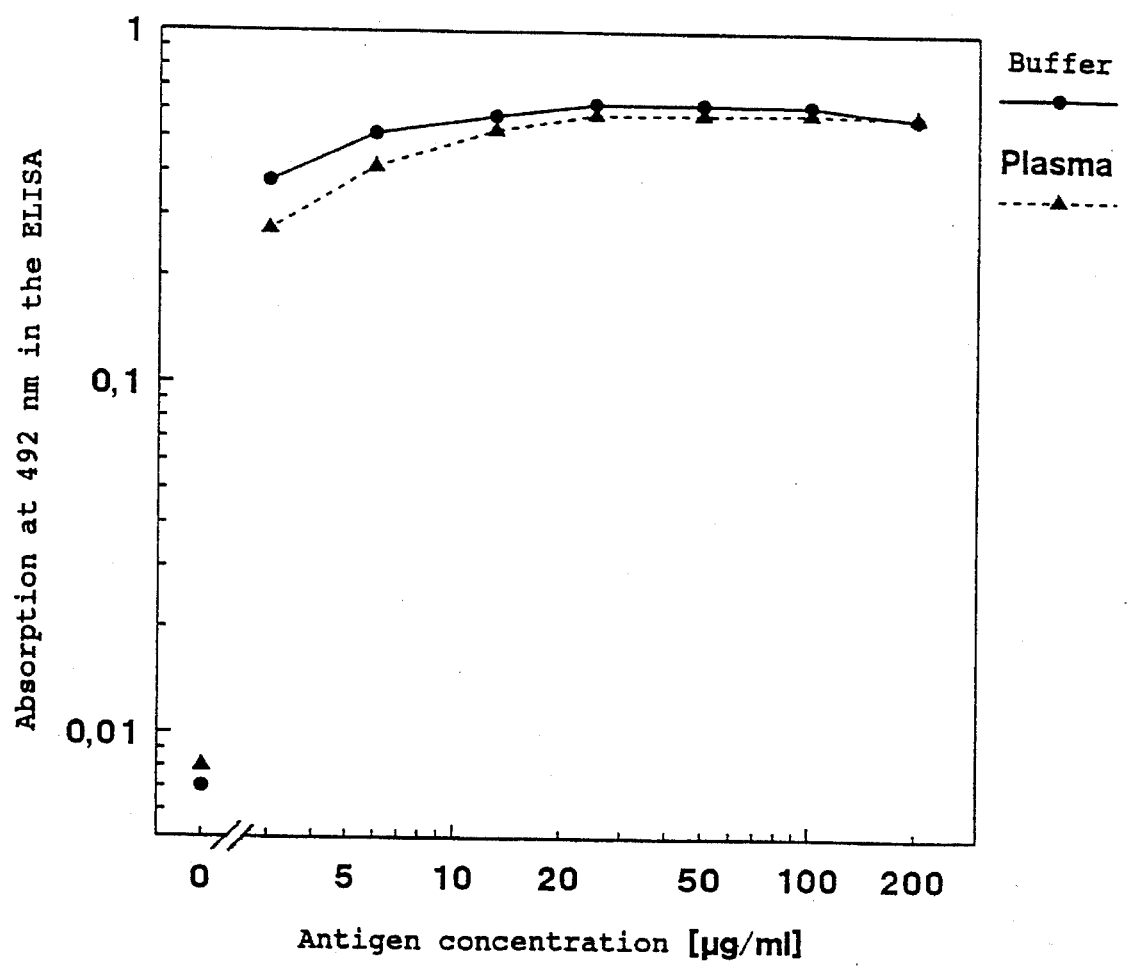
FIGS. 11–13 show the reaction of rabbit antibodies against peptide 3 (SEQ ID NO: 17) with fragment E from fibrinogen (E3) in sample buffer and in human plasma in an ELISA.
Figure 12:
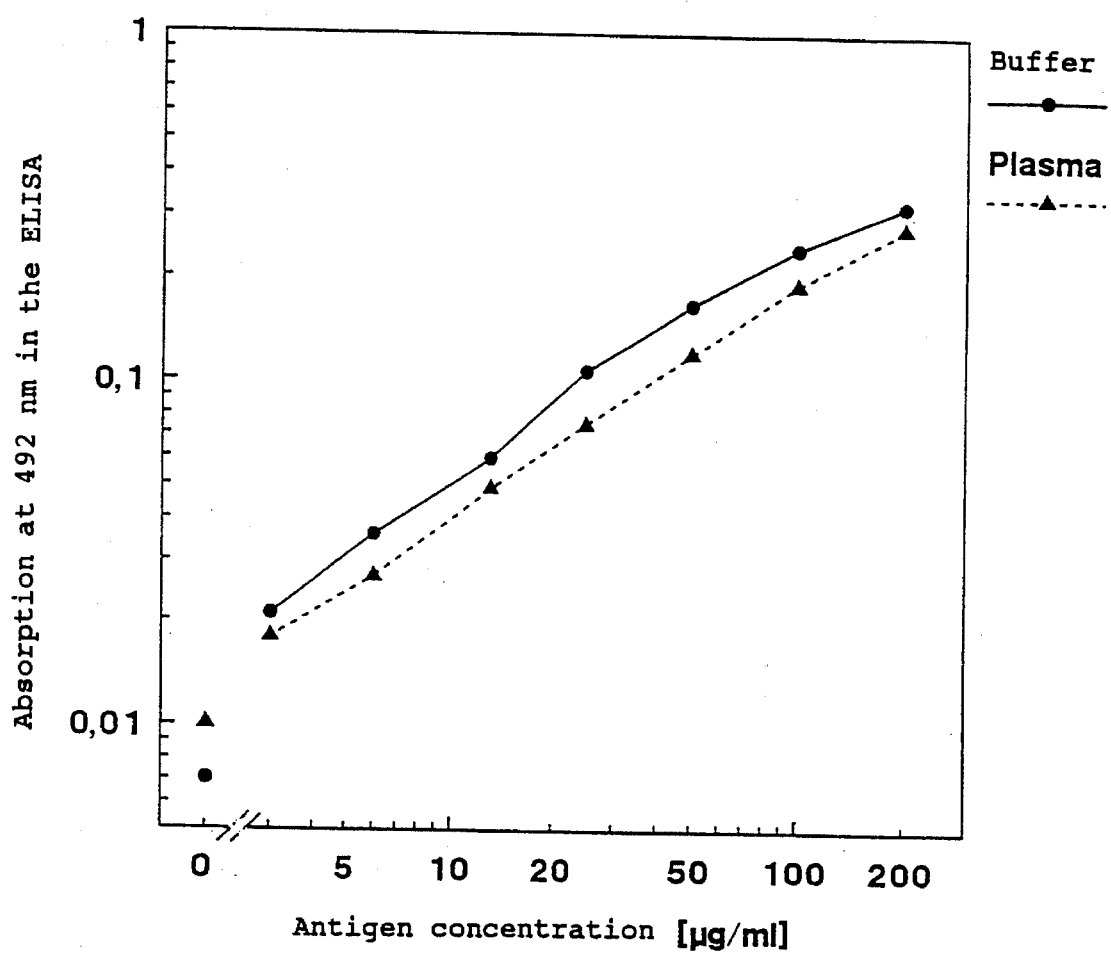
Figure 13:
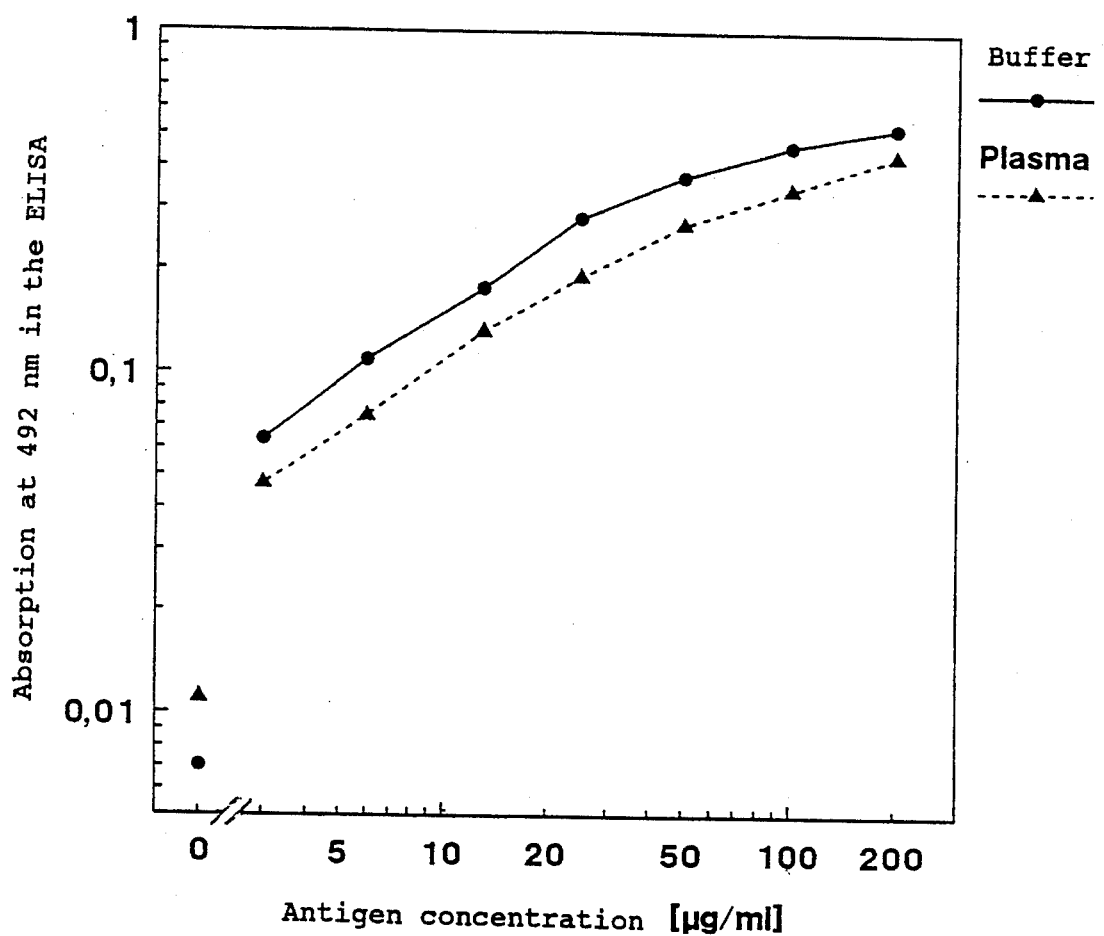

FIG. 11: antibody purified against PP1 (SEQ ID NO: 15).
FIG. 12: antibody purified against PP2 (SEQ ID NO: 16).
FIG. 13: antibody purified against PP3 (SEQ ID NO: 18).

FIGS. 14–16:

Kinetics of the in-vitro formation of fibrinogen cleavage products.

Equal quantities of plasmin were added to human plasma from normal blood donors (SHP) and to plasma which was deficient in α2-antiplasmin (α2AP-DP) and the appearance of fibrinogen cleavage products was followed in the ELISA. The antibodies described in the legend to FIGS. 1–5 were used on the solid phase of the ELISA. The signals shown are those measured in the ELISA for plasma samples incubated with plasmin for different lengths of time.

Figure 14:
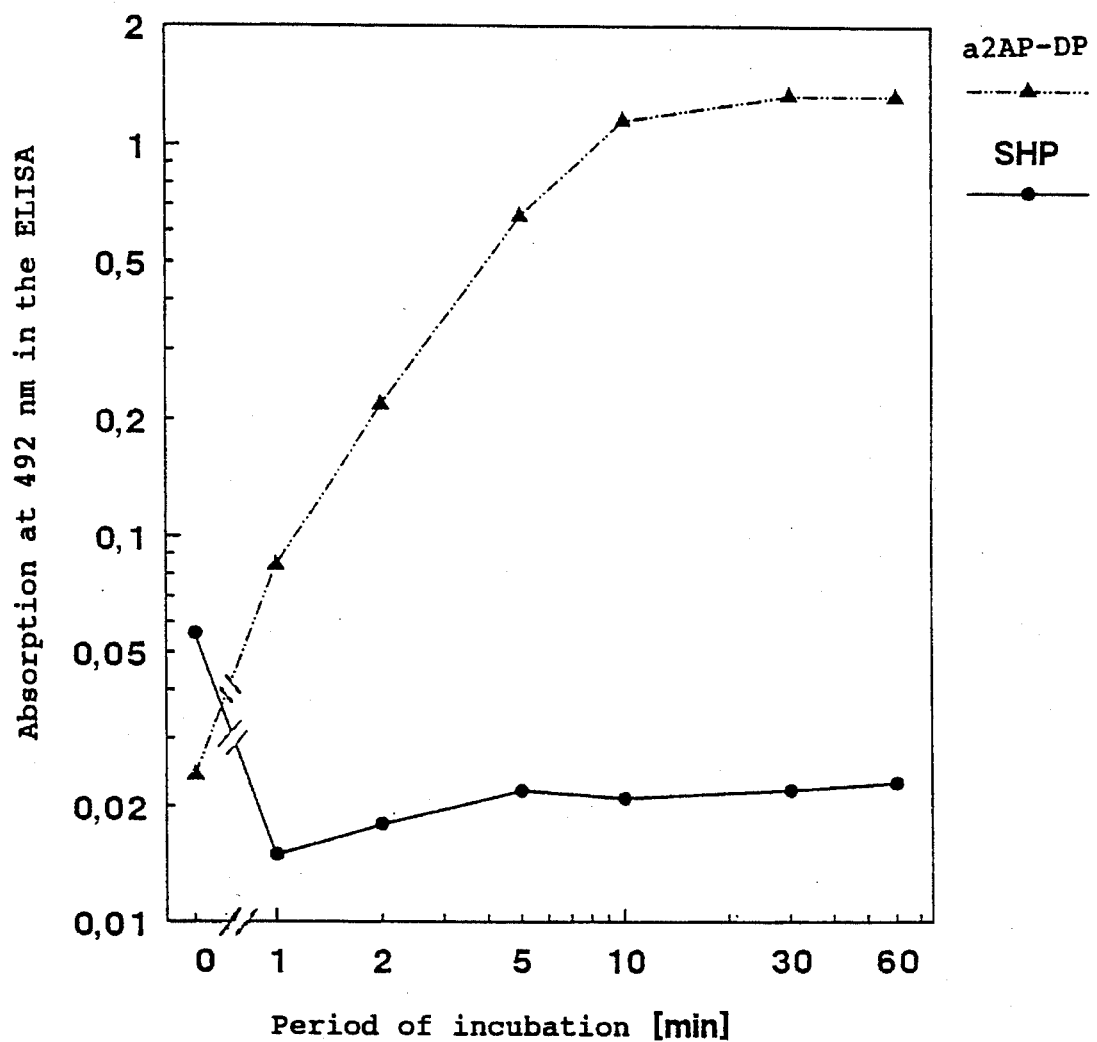
FIGS. 14–16 show the kinetics of the in-vitro formation of fibrinogen products.
Figure 15:
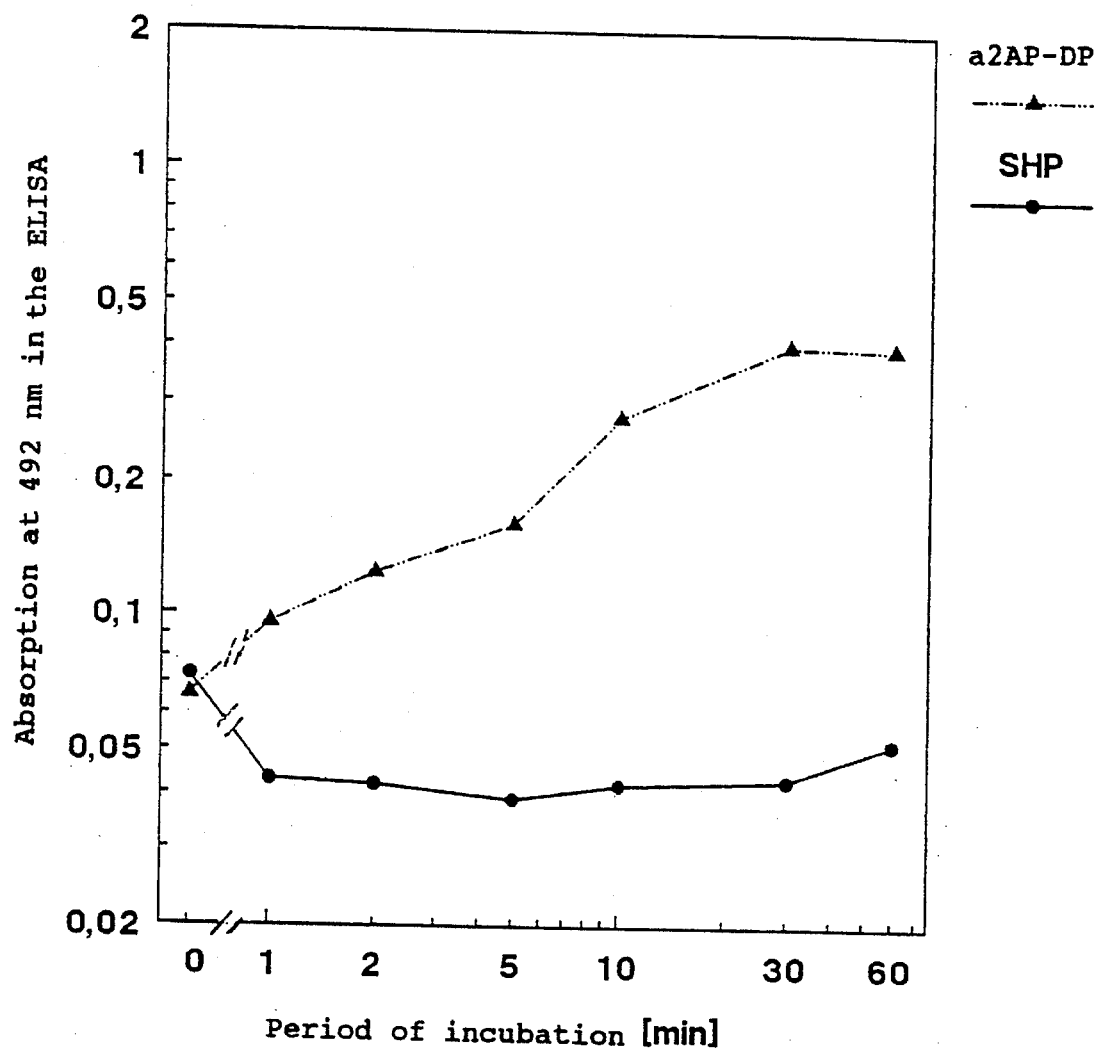
Figure 16:
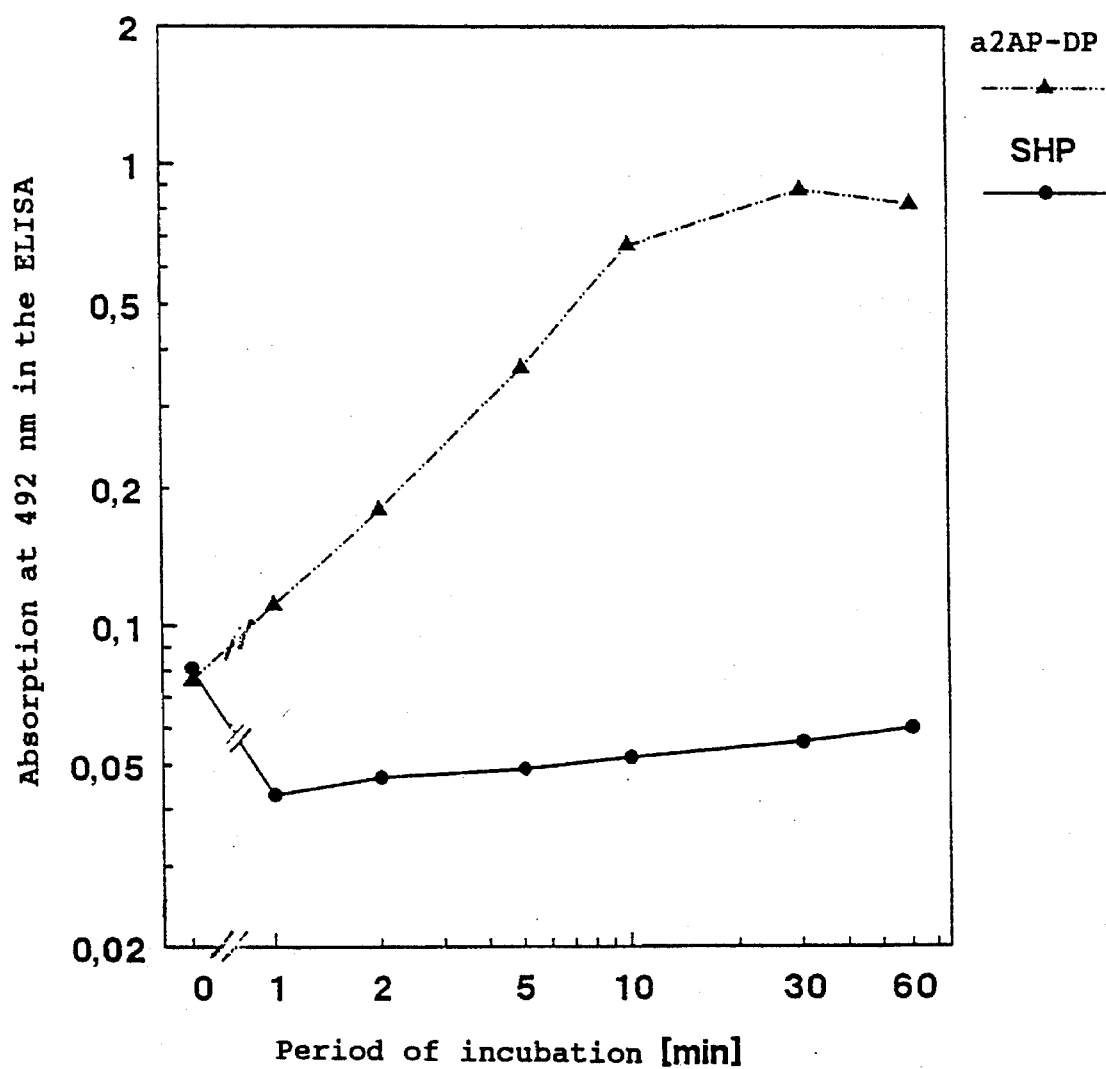

FIG. 14: antibody purified against PP1 (SEQ ID NO: 15).
FIG. 15: antibody purified against PP2 (SEQ ID NO: 16).
FIG. 16: antibody purified against PP3 (SEQ ID NO: 17).

---

---

We claim:

1. An antibody which binds to fibrinogen fragments E1, E2 and E3 which is obtained by immunizing a mammal with a peptide of amino acid SEQ ID NO: 14.

2. The antibody of claim 1 which is purified by immunoadsorption utilizing an immobilized purified peptide of amino acid SEQ ID NO: 17.

3. The antibody of claim 1 which is a monoclonal antibody.

4. An immunochemical method for detecting proteins carrying at least one copy of an epitope which is common to fibrinogen fragments E1, E2 and E3 which comprises the steps of:

(i) contacting a first antibody according to claim 1 with a sample suspected of containing the proteins to form antibody-protein complexes; and (ii) detecting the presence or absence of the antibody-protein complexes thereby detecting the presence or absence of said proteins.

5. The method of claim 4 which is a heterogenous immunoassay.

6. The method of claim 5 wherein an enzyme is used as a label.

7. The method of claim 4 which is a homogenous assay.

8. The method as claimed in claim 7 wherein a particulate, water-insoluble support is used and the presence or absence of antibody-protein complexes is determined by an agglutination reaction which is measured nephelometrically or turbidimetrically.

9. The method of claim 7 wherein the homogenous assay is a particle boosted, nephelometric or turbidimetric assay.

10. The method claim 4 wherein the first antibody is bound to a solid phase and carries a detectable label.

11. The method of claim 10 wherein microfiltration plates are used as the solid phase and the detectable label is a fluorogenic or luminescent dye or an enzyme.

12. The method of claim 4 wherein the presence or absence of the antibody-protein complexes is detected by using a second antibody specific for the same epitope as the first antibody.

13. The method of claim 4 wherein the first antibody is a monospecific antibody and is the only antibody used in the method.

* * * * *